(12) United States Patent
Choi et al.

(10) Patent No.: US 10,959,872 B2
(45) Date of Patent: Mar. 30, 2021

(54) MOTION ASSISTANCE APPARATUS

(71) Applicant: Samsung Electronics Co., Ltd., Suwon-si (KR)

(72) Inventors: Hyun Do Choi, Yongin-si (KR); Jeonghun Kim, Suwon-si (KR); Se-Gon Roh, Suwon-si (KR); Youngbo Shim, Seoul (KR); Minhyung Lee, Seoul (KR); Youn Baek Lee, Yongin-si (KR); Jongwon Lee, Suwon-si (KR); Byungjune Choi, Gunpo-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 359 days.

(21) Appl. No.: 15/945,824

(22) Filed: Apr. 5, 2018

(65) Prior Publication Data
US 2019/0038448 A1 Feb. 7, 2019

(30) Foreign Application Priority Data

Aug. 2, 2017 (KR) .................. 10-2017-0098199
Dec. 27, 2017 (KR) .................. 10-2017-0181120

(51) Int. Cl.
*A61F 5/01* (2006.01)
*A61H 3/00* (2006.01)
*A61H 1/02* (2006.01)

(52) U.S. Cl.
CPC ......... *A61F 5/0127* (2013.01); *A61H 1/0262* (2013.01); *A61H 1/0266* (2013.01);
(Continued)

(58) Field of Classification Search
CPC ...... A61H 1/00; A61H 1/0237; A61H 1/0266; A61H 1/0262; A61H 3/00; A61H 3/008;
(Continued)

(56) References Cited

U.S. PATENT DOCUMENTS 5,215,508 A 6/1993 Bastow
6,171,272 B1 * 1/2001 Akita .................. A61F 5/0127
602/27
(Continued)

FOREIGN PATENT DOCUMENTS

FR 3034660 A1 10/2016
KR 10-2014-0134477 A 11/2014
KR 10-2015-0117539 A 10/2015

OTHER PUBLICATIONS

Extended European Search Report issued by the European Patent Office dated Dec. 4, 2018 for the corresponding EP Patent Application No. 18185877.0.
(Continued)

*Primary Examiner* — Rachel T Sippel
*Assistant Examiner* — Benjamin M. Kusiak
(74) *Attorney, Agent, or Firm* — Harness, Dickey and Pierce, P.L.C.

(57) ABSTRACT

A motion assistance apparatus includes a proximal support configured to support a proximal part of a user, a first drive link and a second drive link configured to perform translational motions with respect to the proximal support at different velocities, a support joint rotatably connected to the second drive link, a support body connecting the first drive link and the support joint, the support body configured to simultaneously perform a translational motion and a rotational motion with respect to the proximal support, a distal support connected to the support body, the distal support configured to support a distal part of the user, and a torque providing device configured to provide a torque to rotate the support joint.

18 Claims, 25 Drawing Sheets

(52) U.S. Cl.
CPC .............. *A61H 3/00* (2013.01); *A61F 5/0193* (2013.01); *A61F 2005/0146* (2013.01); *A61F 2005/0165* (2013.01); *A61H 2001/027* (2013.01); *A61H 2201/0192* (2013.01); *A61H 2201/0196* (2013.01); *A61H 2201/1215* (2013.01); *A61H 2201/1246* (2013.01); *A61H 2201/149* (2013.01); *A61H 2201/164* (2013.01); *A61H 2201/165* (2013.01); *A61H 2201/1642* (2013.01); *A61H 2201/1671* (2013.01); *A61H 2201/1673* (2013.01); *A61H 2201/5005* (2013.01); *A61H 2201/5007* (2013.01); *A61H 2201/5064* (2013.01); *A61H 2201/5069* (2013.01); *A61H 2203/0406* (2013.01); *A61H 2205/10* (2013.01)

(58) Field of Classification Search
CPC ...... A61H 2001/0207; A61H 2001/027; A61H 2205/10; A61H 2003/007; A61H 2201/12; A61H 2201/1207; A61H 2201/1215; A61H 2201/123; A61H 2201/164; A61H 2201/5007; A61H 2201/5064; A61H 2201/5069; A61H 2201/5079; A61H 2203/0406
USPC ............................................................ 601/5
See application file for complete search history.

(56) References Cited

U.S. PATENT DOCUMENTS

| | | | |
|---|---|---|---|
| 7,628,766 B1* | 12/2009 | Kazerooni | A61F 5/00 602/16 |
| 9,101,451 B2 | 8/2015 | Chugunov | |
| 10,610,384 B2* | 4/2020 | Byars | A61F 2/6607 |
| 2006/0069336 A1 | 3/2006 | Krebs et al. | |
| 2008/0304935 A1* | 12/2008 | Scott | A61H 1/0262 414/5 |
| 2012/0143112 A1* | 6/2012 | Tomiyama | A61F 5/0125 602/27 |
| 2012/0259429 A1* | 10/2012 | Han | A61H 3/008 623/24 |
| 2013/0045777 A1 | 2/2013 | Yang et al. | |
| 2013/0046218 A1 | 2/2013 | Wiggin et al. | |
| 2014/0088729 A1 | 3/2014 | Herr et al. | |
| 2015/0085608 A1 | 3/2015 | Tenghamn et al. | |
| 2015/0209214 A1 | 7/2015 | Herr et al. | |
| 2015/0321341 A1 | 11/2015 | Smith | |
| 2016/0067075 A1* | 3/2016 | Malinowski | A61F 5/0113 602/28 |
| 2016/0067137 A1 | 3/2016 | Little et al. | |
| 2016/0098354 A1 | 4/2016 | Hampel et al. | |
| 2016/0278948 A1 | 9/2016 | Piercy et al. | |
| 2017/0165088 A1* | 6/2017 | Lefeber | A61F 2/6607 |
| 2018/0055712 A1* | 3/2018 | Gayral | A61H 1/024 |
| 2018/0104075 A1* | 4/2018 | Mooney | A61F 5/01 |
| 2018/0298973 A1* | 10/2018 | Liao | F16F 1/3821 |

OTHER PUBLICATIONS

Steven H. Collins, et al., "Reducing the energy cost of human walking using an unpowered exoskeleton", Nature, 2015.
Mooney, L. M., Rouse, E. J. & Herr, H. M. "Autonomous exoskeleton reduces metabolic sot of human walking during load carriage", J. Neuroeng. Rehabil. 11, 1-6 (2014).
Malcolm, P., Derave, W., Galle, S. & De Clercq, D. "A Simple Exoskeleton That Assists Flantarilexion Can Reduce the Metabolic Cost of Human Walking", PLoS ONE 8, e56137 (2013).
Sawicki, G. S. & Ferris, D. P. "Mechanics and energetics of level walking with powered ankle exoskeletons", J. Exp. Biol. 211, 1402-1413 (2008).

* cited by examiner

MOTION ASSISTANCE APPARATUS

CROSS-REFERENCE TO RELATED APPLICATIONS

This application claims under 35 U.S.C. § 119 to Korean Patent Application No. 10-2017-0098199, filed on Aug. 2, 2017, and Korean Patent Application No. 10-2017-0181120, filed on Dec. 27, 2017, in the Korean Intellectual Property Office, the entire contents of each of which are incorporated herein by reference in their entirety.

BACKGROUND

1. Field

At least one example embodiment relates to a motion assistance apparatus.

2. Description of the Related Art

With the onset of rapidly aging societies, an increasing number of people may experience inconvenience and/or pain from joint problems. Thus, there may be a growing interest in walking assistance apparatuses enabling the elderly and/or patients having joint problems to walk with less effort.

SUMMARY

Some example embodiments relate to a motion assistance apparatus.

In some example embodiment, the motion assistance apparatus includes a proximal support configured to support a proximal part of a user; a first drive link and a second drive link, the first drive link configured to perform a translational motion with respect to the proximal support at a first velocity and the second drive link configured to perform a translational motion with respect to the proximal support at a second velocity, the first velocity being different from the second velocity; a support joint rotatably connected to the second drive link; a support body connecting the first drive link and the support joint, the support body configured to simultaneously perform a translational motion and a rotational motion with respect to the proximal support; a distal support connected to the support body, the distal support configured to support a distal part of the user; and a torque providing device configured to provide a torque to rotate the support joint.

In some example embodiments, the motion assistance apparatus further includes a coupling link rotatably connected to the proximal support, first drive link and the second drive link, the coupling link configured to rotate about the proximal support; and a connecting link rotatably connected to the proximal support and the second drive link, the connecting link configured to rotate about the proximal support, wherein the first velocity is greater than the second velocity such that the first drive link is configured to perform the translation motion with respect to the proximal support at a faster velocity than the second drive link.

In some example embodiments, the torque providing device includes an elastic body configured to deform in response to rotation of the support joint about the second drive link.

In some example embodiments, the motion assistance apparatus includes an upward protrusion configured to protrude from the support joint, wherein the elastic body is configured to connect the upward protrusion of the support joint and the second drive link.

In some example embodiments, the motion assistance apparatus includes an inversion protrusion configured to protrude from the support joint in an inward direction of the user, the inward direction extending towards a sagittal plane of the user, wherein the elastic body includes an inversion elastic body configured to connect the inversion protrusion of the support joint and the second drive link.

In some example embodiments, the motion assistance apparatus includes an eversion protrusion configured to protrude from the support joint in an outward direction of the user, the outward direction extending away from the sagittal plane of the user, wherein the elastic body further includes an eversion elastic body configured to connect the eversion protrusion of the support joint and the second drive link.

In some example embodiments, an elasticity coefficient of the inversion elastic body is greater than an elasticity coefficient of the eversion elastic body.

In some example embodiments, the torque providing device includes a sub-actuator configured to provide a rotational power to the support joint to rotate the support joint.

In some example embodiments, the support joint includes a first sub-bevel gear, and the sub-actuator includes a second sub-bevel gear, the second sub-bevel gear configured to engage with the first sub-bevel gear.

In some example embodiments, the sub-actuator is parallel to a longitudinal direction of the proximal support.

In some example embodiments, an angle between a shaft of the first sub-bevel gear and a shaft of the second sub-bevel gear is greater than 90 degrees.

In some example embodiments, the motion assistance apparatus further includes a sensor configured to sense motion state information of the user; and a controller configured to control the sub-actuator based on the motion state information.

In some example embodiments, the motion assistance apparatus includes an actuator rotatably connected to the proximal support, the actuator configured to generate power; and a power transmitting rod configured to transmit the power from the actuator to the support body.

In some example embodiments, the actuator includes a drive housing rotatably connected to the proximal support; a drive motor attached to the drive housing, the drive motor configured to generate the power; and a guide configured to extend from the drive housing, and to guide sliding of the power transmitting rod.

In some example embodiments, the support body is configured to rotate about a remote center of motion (RCM), the RCM being in a vicinity of a talocrural joint of the user, when the user wears the motion assistance apparatus.

In some example embodiments, the support body is positioned in a front side of the user when the user wears the motion assistance apparatus.

Some other example embodiments relate to a motion assistance apparatus.

In some example embodiments, the motion assistance apparatus includes a proximal support; a first drive link and a second drive link, the first drive link configured to perform a translational motion with respect to the proximal support at a first velocity and the second drive link configured to perform a translational motion with respect to the proximal support at a second velocity, the first velocity being different from the second velocity; a support body having a first end and a second end, the first end of the support body and the second end of the support body rotatably connected to the first drive link and the second drive link, respectively, the support body configured to simultaneously perform a translational motion and a rotational motion with respect to the proximal support; a distal support rotatably connected to the support body; and a torque providing device configured to provide a torque to rotate the distal support.

In some example embodiments, the torque providing device includes an elastic body configured to connect the support body and the distal support, and to deform in response to rotation of the distal support about the support body.

In some example embodiments, the motion assistance apparatus includes a protrusion configured to protrude from the support body toward an inner portion of a foot of a user, the protrusion configured to support a first end of the elastic body, wherein the distal support includes a connecting part configured to cover an outer portion of the foot of the user, and to support a second end of the elastic body.

Some example embodiments relate to a support link of a motion assistance apparatus.

In some example embodiments, the support link includes a joint; a body connected having a first portion, a second portion and third portion, the first portion being connected to the joint, the second portion being rotatably connected to a power transmitting rod and a first drive link, and the third portion being connected to a distal support, the distal support configured to support a distal part of a user and to rotate in at least a first direction and a second direction, the second direction being opposite the first direction; a first protrusion; and a torque providing device connected between the first protrusion and a second drive link, the second drive link being connected to the joint along with the first portion of the body, the torque providing device configured to exert a torque on the first protrusion when the distal support rotates in the first direction, the torque urging the body to rotate about the joint such that the distal support connected to the third portion of the body is urged to rotate in the second direction.

In some example embodiments, the torque providing device includes a first elastic body configured to elastically connect the first protrusion and the second drive link, the first elastic body having a first elastic coefficient; an inversion elastic body configured to elastically connect a second protrusion and the second drive link, the second protrusion protruding from the joint in an upward direction with respect to the distal support, the inversion elastic body having a second elastic coefficient; and an eversion elastic body configured to elastically connect a third protrusion and the second drive link, the third protrusion protruding from the joint in an inward direction of the user, the inward direction extending towards a sagittal plane of the user, the eversion elastic body having a third elastic coefficient, the third elastic coefficient being less than the second elastic coefficient.

In some example embodiments, the joint includes a first sub-bevel gear, and the torque providing device includes a sub-actuator including a second sub-bevel gear, the second sub-bevel gear configured to engage with the first sub-bevel gear, the sub-actuator configured to generate a force and apply the force to the first sub-bevel gear to rotate the joint.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1A:
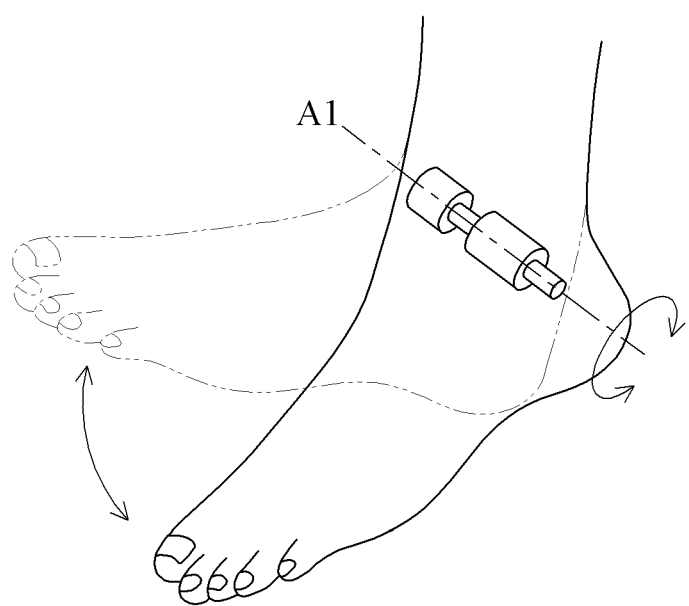
FIG. 1A illustrates a motion of a talocrural joint of a user according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

Hereinafter, the same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 1B:
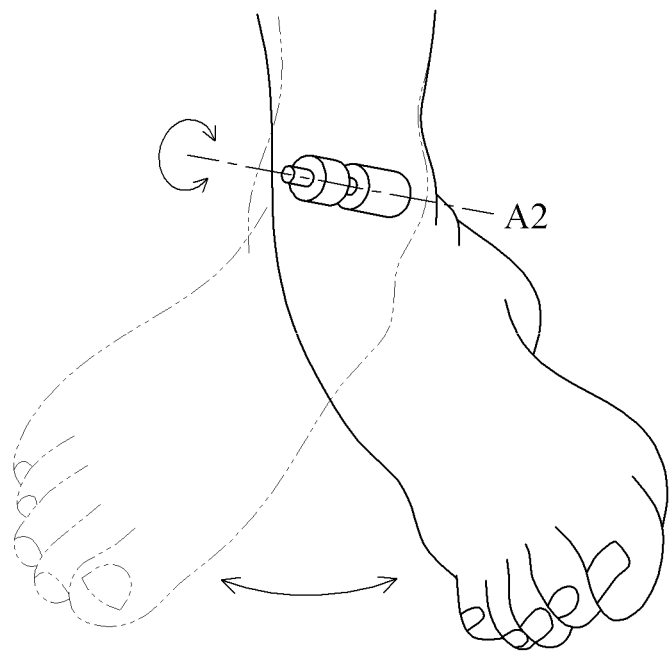
FIG. 1B illustrates a motion of a subtalar joint of a user according to at least one example embodiment.

FIG. 1A illustrates a motion of a talocrural joint of a user, and FIG. 1B illustrates a motion of a subtalar joint of the user.

Referring to FIGS. 1A and 1B, an ankle of the user moves relative to two axes, in detail, a first axis A1 and a second axis A2 conceptually illustrating a talocrural joint and a subtalar joint, respectively. The ankle of the user may perform a dorsi-flexion motion or plantar-flexion motion relative to the talocrural joint. Further, the ankle of the user may perform an eversion motion or inversion motion relative to the subtalar joint. When the ankle of the user moves relative to one of the first axis A1 and the second axis A2, a position or angle of the other of the first axis A1 and the second axis A2 may change. Hereinafter, it is described that a motion assistance apparatus according to at least one example embodiment may enable an ankle of a user to move relative to the first axis A1 and/or the second axis A2.

Figure 2:
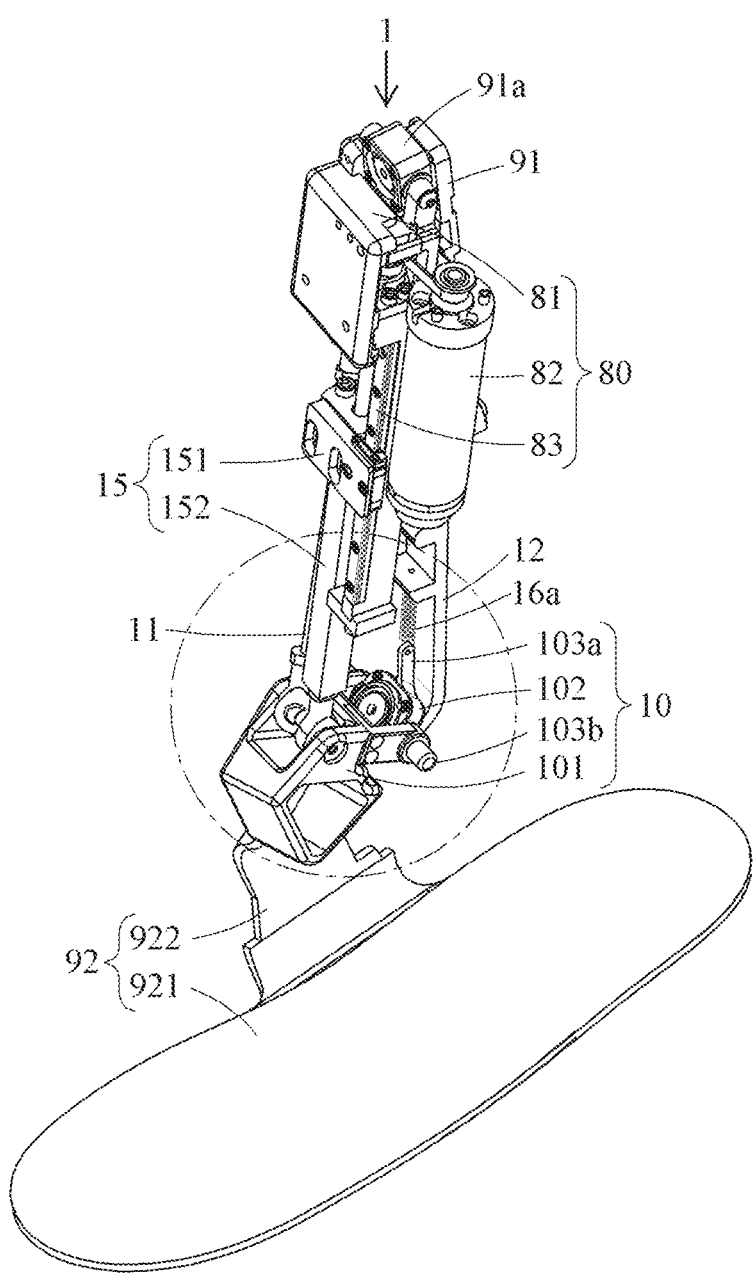
FIG. 2 is a perspective view illustrating a motion assistance apparatus according to at least one example embodiment.
Figure 3:
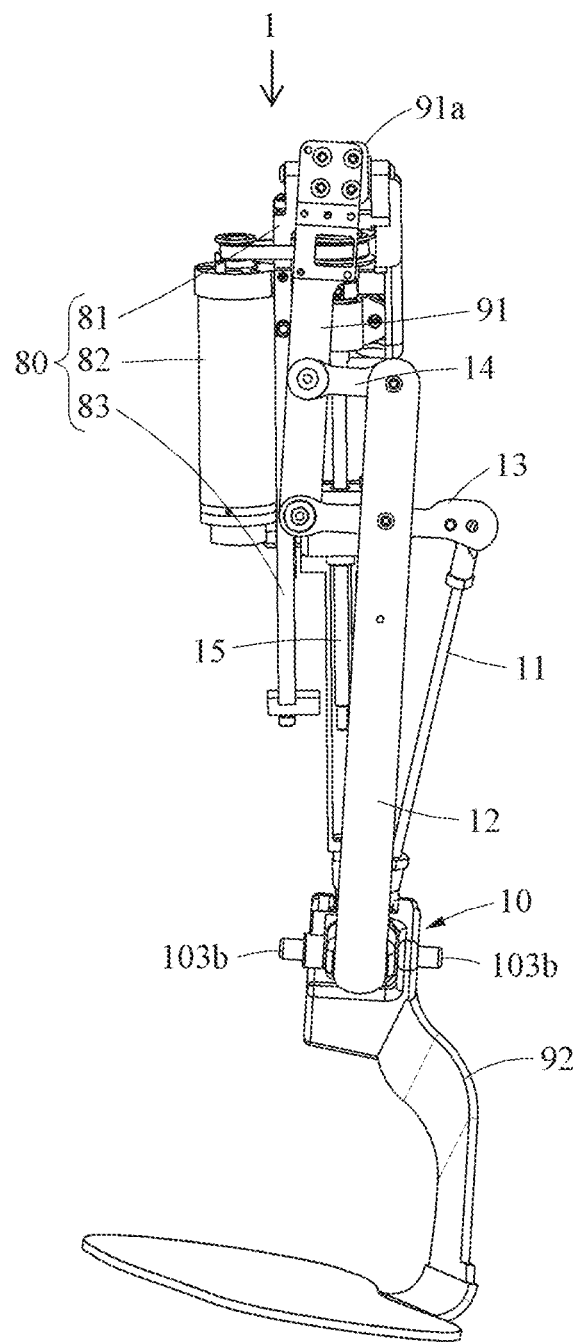
FIG. 3 is a rear view illustrating a motion assistance apparatus according to at least one example embodiment.

FIG. 2 is a perspective view illustrating a motion assistance apparatus according to at least one example embodiment, and FIG. 3 is a rear view of the motion assistance apparatus according to at least one example embodiment.

Referring to FIGS. 2 and 3, a motion assistance apparatus 1 may be worn by a user to assist a motion of the user. The user may correspond to a human, an animal, or a robot. However, the user is not limited thereto. The motion assistance apparatus 1 may include a proximal support 91, a distal support 92, a support link 10, a first drive link 11, a second drive link 12, a coupling link 13, a connecting link 14, a power transmitting rod 15, a first elastic body 16a, and an actuator 80.

The proximal support 91 may support a proximal part of the user, and the distal support 92 may support a distal part of the user. The motion assistance apparatus 1 may assist a joint motion of the user by adjusting an angle between the proximal support 91 and the distal support 92. The proximal support 91 may support a shank of the user, the distal support 92 may support a foot of the user such that the motion assistance apparatus 1 may assist a plantar-flexion motion and/or a dorsi-flexion motion of a talocrural joint of the user. In another example, the proximal support 91 may support a forearm of the user, the distal support 92 may assist a metacarpal of the user such that the motion assistance apparatus 1 may assist a flexion motion and/or an extension motion of a wrist joint of the user. Hereinafter, a case in which the motion assistance apparatus 1 assists a motion of the talocrural joint will be described. However, the joint assisted by the motion assistance apparatus 1 is not limited to the talocrural joint.

The proximal support 91 may be attached to the shank of the user. The proximal support 91 may include a calf attachable part (not shown) configured to enclose a calf of the user. A circumference of the calf attachable part may be adjusted based on a size of the calf of the user. The calf attachable part may be an elastic band. The proximal support 91 may be attached to a front side of the shank of the user.

The distal support 92 may be attached to the foot of the user. As shown in the drawings, the distal support 92 may have a structure to be attached to an outer surface of a shoe that the user wears, or to be inserted into the shoe. The distal support 92 may include an insole part 921 configured to support a sole of the foot of the user, and a connecting part 922 configured to cover a side of the foot of the user and connected to the support link 10.

As described below, a power of the actuator 80 may be transmitted in an order of the power transmitting rod 15, the support link 10, the first drive link 11, the coupling link 13, and the second drive link 12. In the above power transmitting process, the first drive link 11 and the second drive link 12 may move with respect to the proximal support 91 at different velocities. Thus, the support link 10 connected to the first drive link 11 and the second drive link 12 may simultaneously perform a translational motion and a rotational motion with respect to the proximal support 91.

The motion assistance apparatus 1 may further include, on the proximal support 91, a proximal joint 91a configured to rotatably support the actuator 80 with 2 degree of freedom (DOF). The proximal joint 91a may be a universal joint or a ball joint. The proximal joint 91a may be on an upper side of the proximal support 91.

The actuator 80 may be rotatably connected to the proximal support 91. The actuator 80 may generate the power to drive the motion assistance apparatus 1. The actuator 80 may include a drive housing 81, a drive motor 82, and a guide 83.

The drive housing 81 may rotate with respect to the proximal support 91 with 2 DOF through the proximal joint 91a. The drive housing 81 may rotate about two axes intersecting a longitudinal direction of the proximal support 91. In detail, the drive housing 81 may rotate about an axis perpendicular to a front surface of the proximal support 91, and an axis parallel to the front surface of the proximal support 91. The axis perpendicular to the front surface of the proximal support 91 and the axis parallel to the front surface of the proximal support 91 may be parallel to a sagittal axis and a coronal axis, respectively, when the user is standing.

The drive motor 82 may be fixed to the drive housing 81. The drive motor 82 may generate a power to slide the power transmitting rod 15. The drive motor 82 may be replaceable. The drive motor 82 may be fixed to the drive housing 81 to perform a rigid body motion.

The guide 83 may extend from the drive housing 81. When the user is standing, the guide 83 may extend from the drive housing 81 downward, that is, in a direction toward the distal support 92. The guide 83 may guide sliding of the power transmitting rod 15. The guide 83 may assist the power transmitting rod 15 to slide.

The power transmitting rod 15 may slide using the power received from the actuator 80. The power transmitting rod 15 may slide along the guide 83. The power transmitting rod 15 and the actuator 80 may be connected to each other in the manner of a ball screw. The actuator 80 may slide the power transmitting rod 15 upward or downward. The power transmitting rod 15 may include a power transmitting body 151 and an extension 152.

The power transmitting body 151 may be in direct contact with the guide 83. The power transmitting body 151 may slide in a longitudinal direction of the guide 83.

The extension 152 may be a longitudinal member that extends from a first side of the power transmitting body 151. A first end of the extension 152 may be connected to the power transmitting body 151, and a second end of the extension 152 may be connected to one side of the support link 10. The support link 10 may rotate with respect to the extension 152 with 2 DOF. For example, a universal joint or a ball joint may be between the extension 152 and the support link 10.

The first drive link 11 may perform a translational motion with respect to the proximal support 91. The coupling link 13 may connect the proximal support 91, the first drive link 11, and the second drive link 12 (see FIG. 3). A first end of the first drive link 11 may be rotatably connected to a first end of the coupling link 13 with 2 DOF. For example, a universal joint or a ball joint may be between the first drive link 11 and the coupling link 13. A second end of the first drive link 11 may be rotatably connected to the support link 10 with 2 DOF. For example, a universal joint or a ball joint may be between the first drive link 11 and the support link 10. Meanwhile, the first drive link 11 may simultaneously perform a translational motion and a rotational motion with respect to the proximal support 91.

The second drive link 12 may perform a translational motion with respect to the proximal support 91. The proximal support 91 and the second drive link 12 may be connected by the coupling link 13. The second drive link 12 may be closer to the proximal support 91 than the first drive link 11, and thus the second drive link 12 may perform the translational motion at a slower velocity than the first drive link 11.

The proximal support 91, the second drive link 12, the coupling link 13, and the connecting link 14 may construct a 4-bar linkage structure, thereby implementing a 1-DOF motion. A first end of the connecting link 14 may be rotatably connected to the proximal support 91, and a second end of the connecting link 14 may be rotatably connected to the second drive link 12. The first end of the coupling link 13 may be rotatably connected to the proximal support 91, a middle part of the coupling link 13 may be rotatably connected to the second drive link 12, and a second end of the coupling link 13 may be rotatably connected to the first drive link 11.

The coupling link 13 and the connecting link 14 may be parallel to each other. A distance between an axis of the coupling link 13 rotatably connected to the proximal support 91 and an axis of the coupling link 13 rotatably connected to the second drive link 12 may be equal to a distance between an axis of the connecting link 14 rotatably connected to the proximal support 91 and an axis of the connecting link 14 rotatably connected to the second drive link 12. By the above structure, the second drive link 12 may slide while being parallel to the proximal support 91.

A length of the coupling link 13 may be greater than a length of the connecting link 14. A radius of gyration of the coupling link 13 may be greater than a radius of gyration of the connecting link 14. The second drive link 12 may be rotatably connected to a middle part of the connecting link 13, and the first drive link 11 may be rotatably connected to an end portion of the connecting link 13. By the above structure, when the coupling link 13 rotates, a velocity of the first drive link 11 may be faster than a velocity of the second drive link 12. That is, a relative motion between the first drive link 11 and the second drive link 12 may be implemented.

The support link 10 may simultaneously perform a translational motion and a rotational motion with respect to the proximal support 91. The support link 10 may rotate about a remote center of motion (RCM) in a vicinity of the talocrural joint of the user connecting the shank and the foot of the user. The support link 10 may be on a front side of the user when the user wears the motion assistance apparatus 1. The support link 10 may be in a space above the foot of the user and in front of the shank of the user. The support link 10 may include a support body 101, a support joint 102, and a plurality of protrusions 103a, 103b, and 103c.

A first portion of the support body 101 may be connected to the power transmitting rod 15 and the first drive link 11. A second portion of the support body 101 may be connected to the support joint 102. A third portion of the support body 101 may be connected to the distal support 92 that encloses a top and a sole of the foot in front of an ankle. By the above structure, the support link 10 may rotate about the RCM in the vicinity of the talocrural joint of the user, without being connected to a component on an axis of the talocrural joint of the user. Thus, the support link 10 may perform a motion similar to an actual motion of the talocrural joint of the user, and also enable the user to put on or off a shoe while wearing the motion assistance apparatus 1.

The support joint 102 may connect the support body 101 and the second drive link 12 such that the support body 101 may rotate on the second drive link 12.

The plurality of protrusions 103a, 103b, and 103c may protrude from the support joint 102, and support first ends of elastic bodies 16a and 16b, which will be described later. The plurality of protrusions 103a, 103b, and 103c may include an upward protrusion 103a, an inversion protrusion 103b, and an eversion protrusion 103c.

The inversion protrusion 103b and the eversion protrusion 103c may protrude from the support joint 102 in a direction intersecting a longitudinal direction of the second drive link 12.

The first elastic body 16a may connect the support link 10 and the second drive link 12, and deform when the support link 10 rotates with respect to the second drive link 12. In the example of FIG. 2, the motion assistance apparatus 1 includes the first elastic body 16a connecting the upward protrusion 103a and the second drive link 12. However, the motion assistance apparatus 1 may include the second elastic body 16b connecting the inversion protrusion 103b and the second drive link 12 and/or a third elastic body 16c connecting the eversion protrusion 103c and the second drive link 12. Description thereof will be provided further with reference to FIGS. 8 through 10. The first elastic body 16a may include various materials such as, for example, a compression spring, a tensile spring, a flat spring, a rubber band, and an elastic fiber.

The first elastic body 16a may be in an initial state when the user is standing, and may extend when the ankle of the user performs an inversion motion or an eversion motion. When the distal support 92 rotates about the support link 10, the first elastic body 16a may apply a force to the distal support 92 such that the distal support 92 may be restored to an initial position. That is, when the ankle of the user wearing the motion assistance apparatus 1 performs an inversion motion or an eversion motion, the first elastic body 16a may restore the ankle of the user to the initial state. Such an assistance force may prevent an unintended inversion motion or eversion motion of the ankle of the user, thereby preventing a fall of the user.

Figure 4:
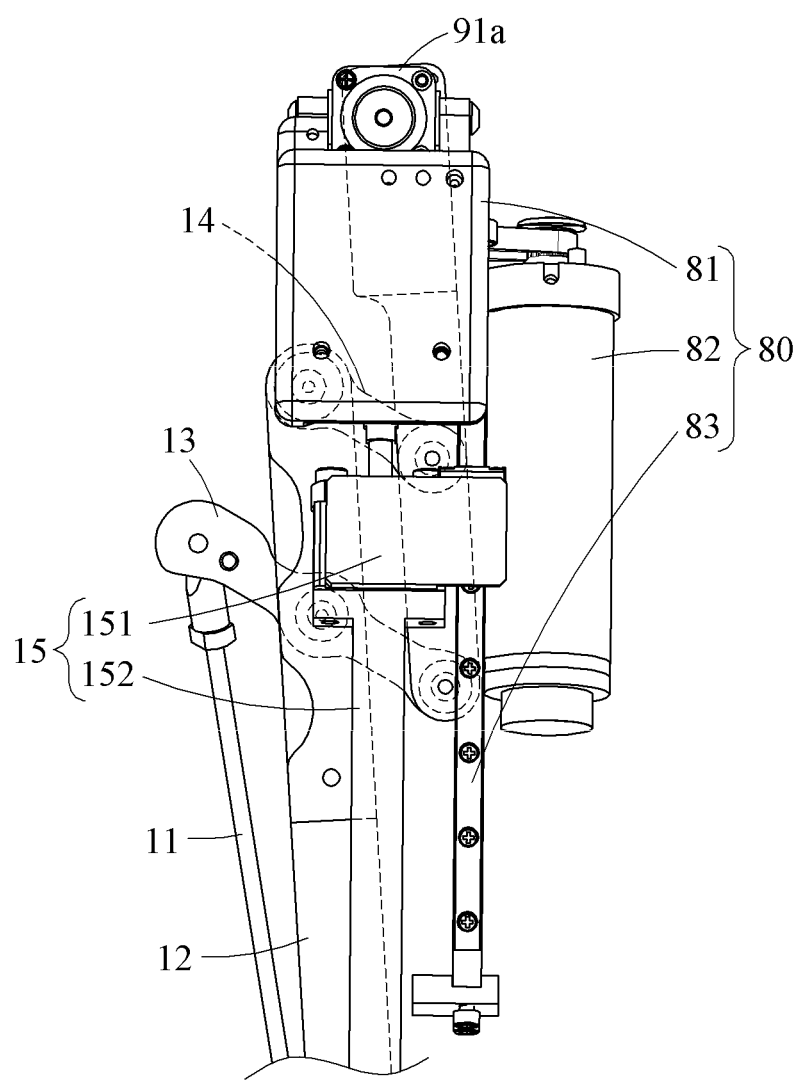
FIG. 4 is a partially enlarged front view illustrating a motion assistance apparatus that assists a dorsi-flexion motion of a talocrural joint of a user according to at least one example embodiment.
Figure 5:
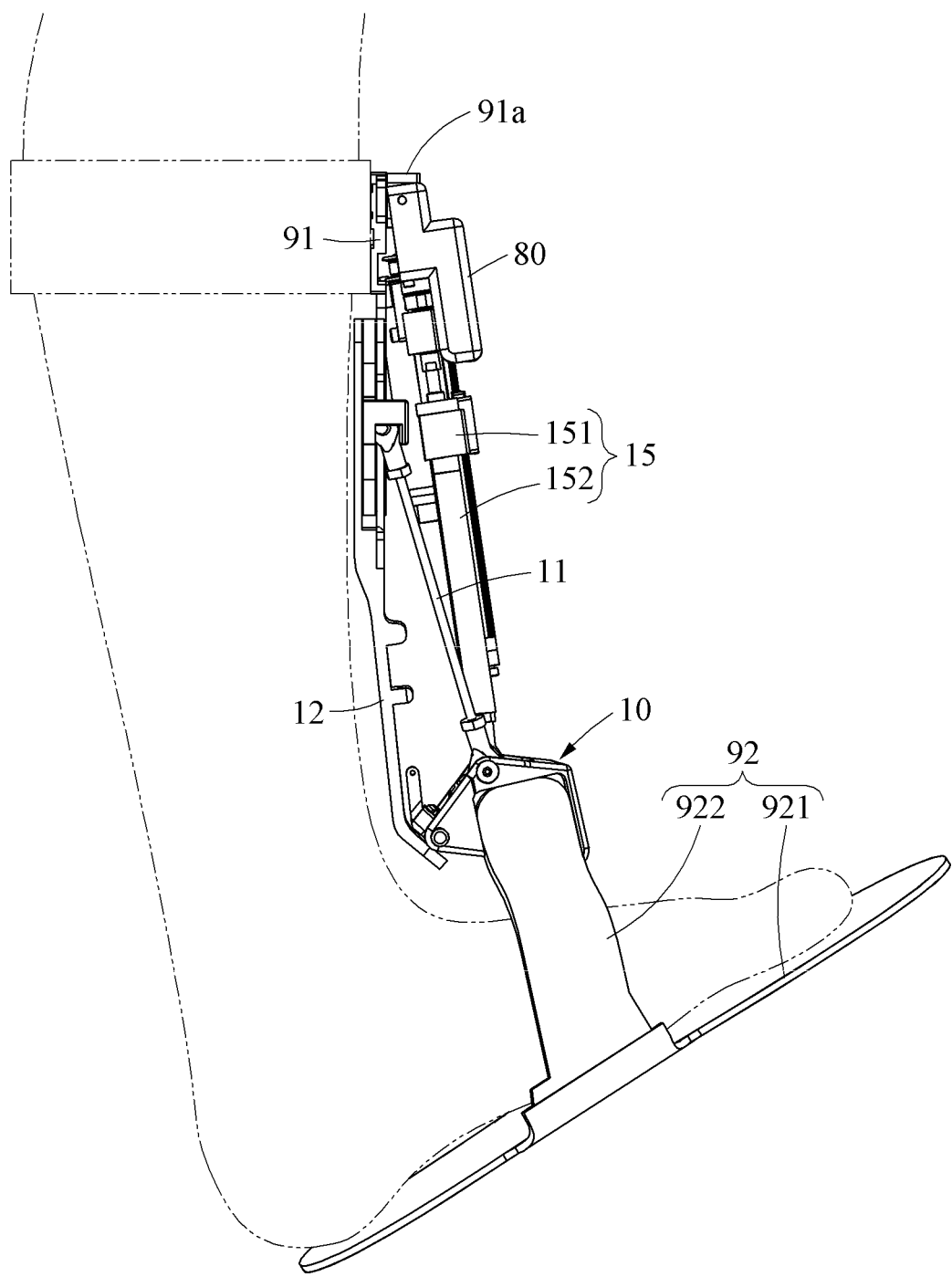
FIG. 5 is a side view illustrating a motion assistance apparatus that assists a dorsi-flexion motion of a talocrural joint of a user according to at least one example embodiment.
Figure 6:
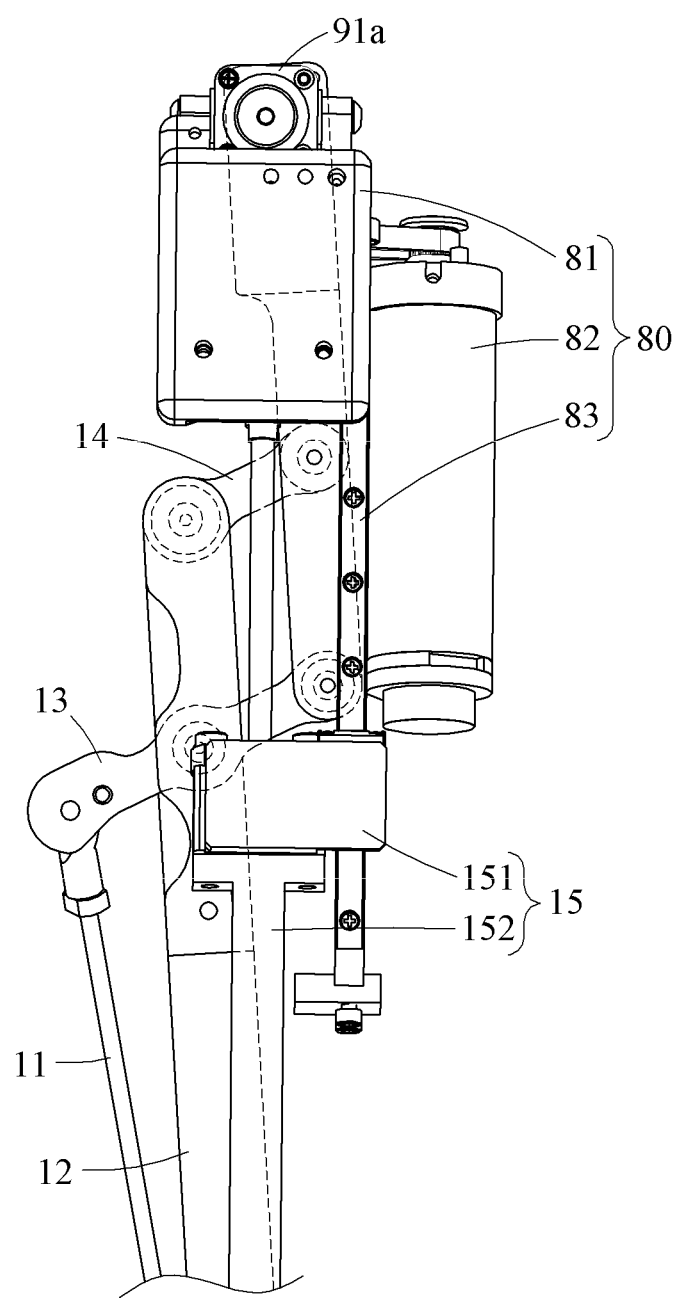
FIG. 6 is a partially enlarged front view illustrating a motion assistance apparatus that assists a plantar-flexion motion of a talocrural joint of a user according to at least one example embodiment.
Figure 7:
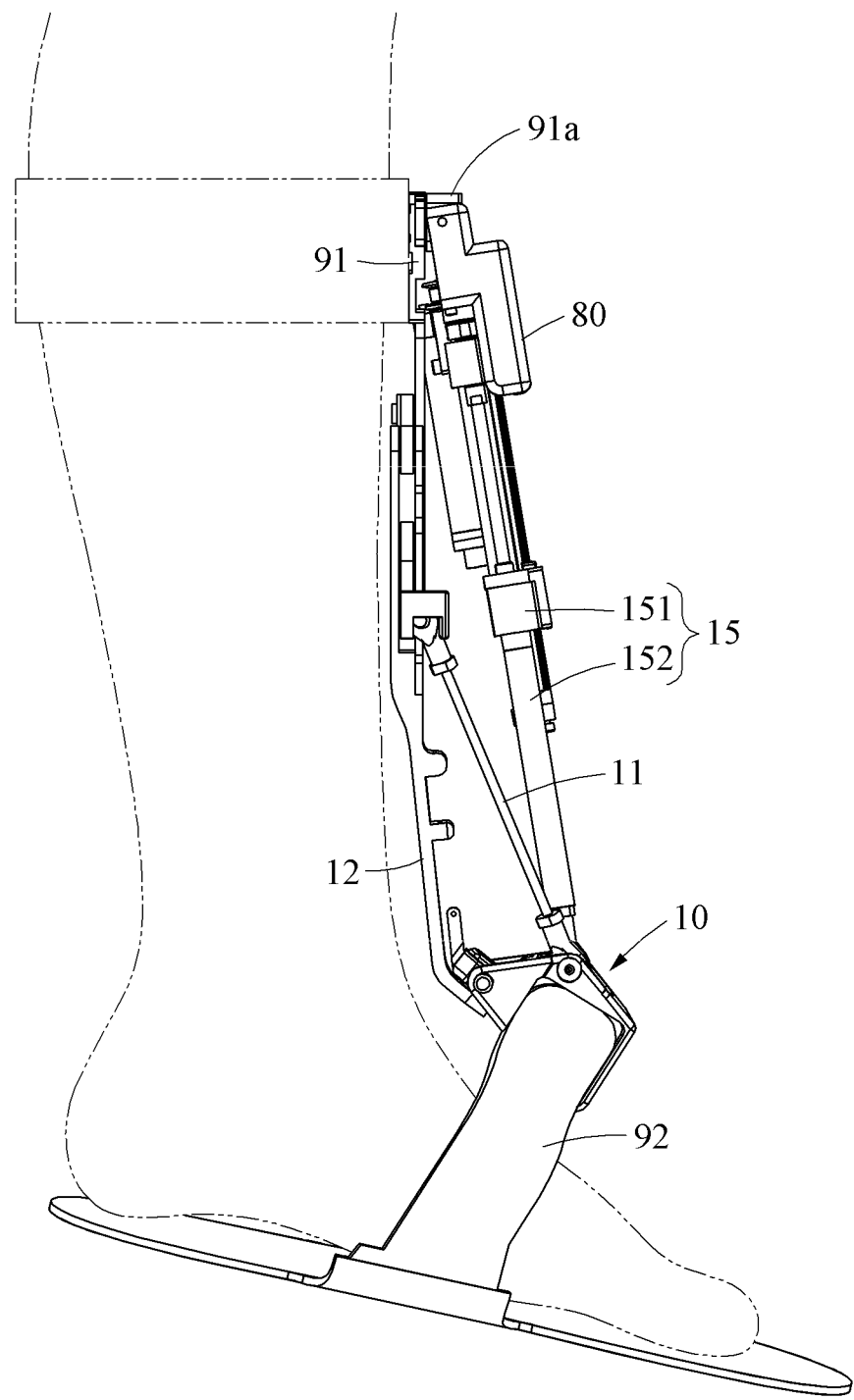
FIG. 7 is a side view illustrating a motion assistance apparatus that assists a plantar-flexion motion of a talocrural joint of a user according to at least one example embodiment.

FIG. 4 is a partially enlarged front view illustrating a motion assistance apparatus that assists a dorsi-flexion motion of a talocrural joint of a user according to at least one example embodiment, FIG. 5 is a side view illustrating the motion assistance apparatus that assists the dorsi-flexion motion of the talocrural joint of the user according to at least one example embodiment, FIG. 6 is a partially enlarged front view illustrating the motion assistance apparatus that assists a plantar-flexion motion of the talocrural joint of the user according to at least one example embodiment, and FIG. 7 is a side view illustrating the motion assistance apparatus that assists the plantar-flexion motion of the talocrural joint of the user according to at least one example embodiment.

Referring to FIGS. 4 through 7, a mechanism in which the motion assistance apparatus 1 assists a plantar-flexion motion of the user will be described. The power transmitting rod 15 may move the support link 10 downward through the actuator 80. In this example, the first drive link 11 connected to the support link 10 may move downward. Since the first drive link 11 and the second drive link 12 are connected by the coupling link 13, the second drive link 12 may also move downward. A displacement of the second drive link 12 may be less than a displacement of the first drive link 11. Thus, the two drive links 11 and 12 may move downward at different velocities, and the support body 101 may rotate forward about the support joint 102. Here, "forward" may refer to a direction in which the user performs the plantar-flexion motion. By the above process, the support link 10 may simultaneously perform a translational motion and a rotational motion with respect to the proximal support 91.

Hereinafter, a mechanism in which the motion assistance apparatus 1 assists a dorsi-flexion motion of the user will be described. The power transmitting rod 15 may move the support link 10 upward through the actuator 80. In this example, the first drive link 11 connected to the support link 10 may move upward. Since the first drive link 11 and the second drive link 12 are connected by the coupling link 13, the second drive link 12 may also move upward. The displacement of the second drive link 12 may be less than the displacement of the first drive link 11. Thus, the two drive links 11 and 12 may move upward at different velocities, and the support body 101 may rotate backward about the support joint 102. Here, "backward" may refer to a direction in which the user performs the dorsi-flexion motion.

Figure 8:
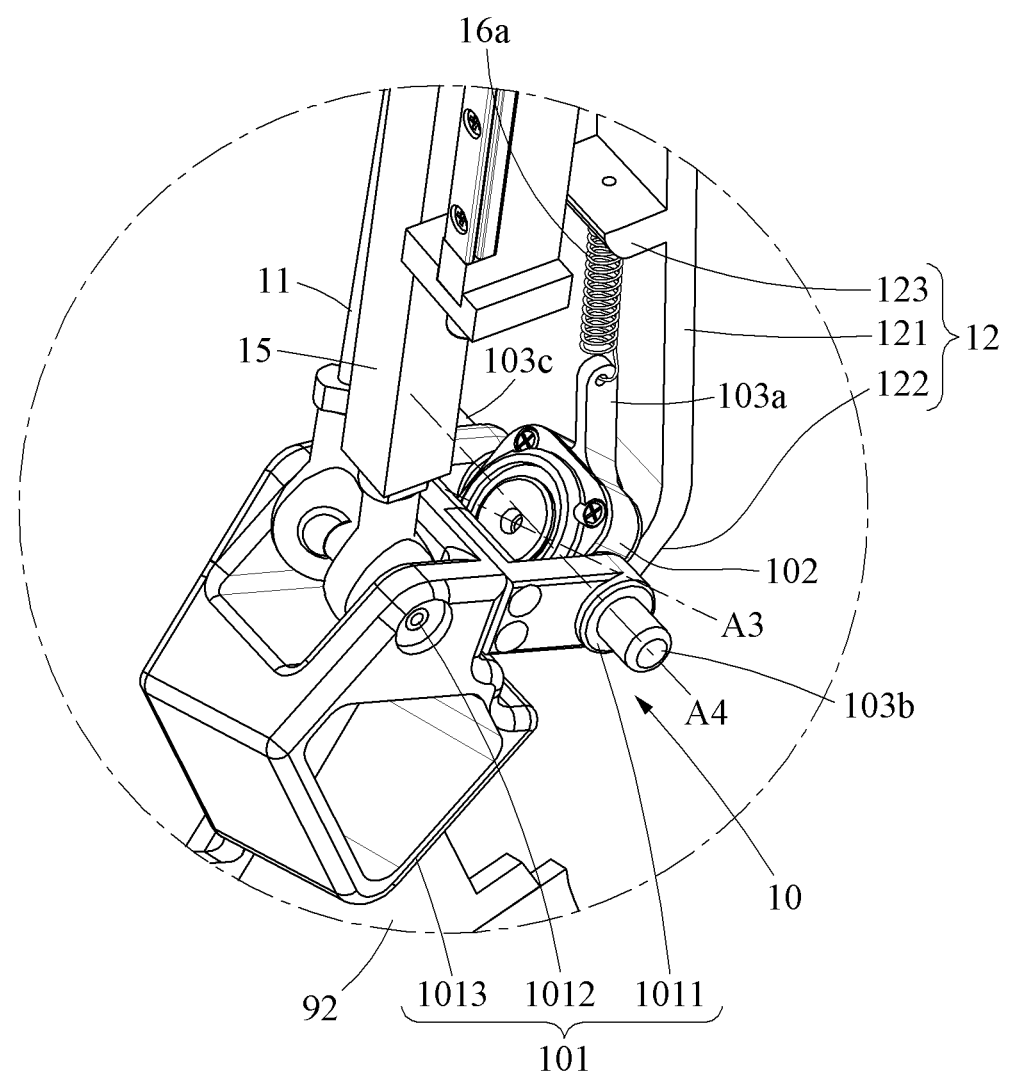
FIG. 8 is a partially enlarged perspective view illustrating a motion assistance apparatus according to at least one example embodiment.

FIG. 8 is a partially enlarged perspective view illustrating a motion assistance apparatus according to at least one example embodiment.

Referring to FIG. 8, the support link 10 may include the support body 101 and the support joint 102. The second drive link 12 may be a longitudinal member parallel to the proximal support 91 of FIG. 2. The second drive link 12 may include a link body 121, a link bent portion 122 bent from the link body 121 toward a front side thereof, and a link projection 123 protruding from the link body 121 toward the front side thereof.

The support joint 102 may be rotatably connected to the second drive link 12. The support joint 102 may be rotatably connected to the link bent portion 122 of the second drive link 12. When the user wears the motion assistance apparatus 1 of FIG. 2, a third axis A3 which is a rotation axis of the support joint 102 may be the same as or substantially parallel to the second axis A2 of FIG. 1B which is a rotation axis of the subtalar joint of the user. By the above structure, the distal support 92 of FIG. 2 may rotate in compliance with a motion of the subtalar joint of the user.

The upward protrusion 103a may protrude from the support joint 102 upward, for example, in a direction toward the link projection 123, and the first elastic body 16a may be connected to the upward protrusion 103a. By the above structure, when compared to a case in which the first elastic body 16a is connected directly to the support joint 102, the length of the first elastic body 16a may change relatively greatly based on an angle of rotation of the support joint 102. Thus, a relatively great elastic force may be provided even using the first elastic body 16a with a relatively low elasticity coefficient.

The inversion protrusion 103b and the eversion protrusion 103c may protrude from the support joint 102 in a direction orthogonal to the third axis A3. The inversion protrusion 103b and the eversion protrusion 103c may protrude from the support joint 102 in a direction intersecting the longitudinal direction of the second drive link 12. The inversion protrusion 103b and the eversion protrusion 103c may be on a left side and a right side of the support joint 102, respectively from the point of view of the wearer. The inversion protrusion 103b and the eversion protrusion 103c may be parallel to a fourth axis A4 which is a rotation axis of the support body 101.

The inversion protrusion 103b may protrude from the support joint 102 in an inward direction of the user. Here, the "inward direction of the user" may be construed as a direction toward a longitudinal axis penetrating through a top of a head of the user, or a direction toward a sagittal plane penetrating through a center of the user.

The eversion protrusion 103c may protrude from the support joint 102 in an outward direction of the user. Here, the "outward direction of the user" may be construed as a direction away from the longitudinal axis penetrating through the top of the head of the user, or a direction away from the sagittal plane penetrating through the center of the user.

The support body 101 may include a first portion 1011 rotatably connected to the support joint 102, a second portion 1012 rotatably connected to the power transmitting rod 15 and the first drive link 11, and a third portion 1013 connected to the distal support 92. The fourth axis A4 which is the rotation axis of the support body 101 may be orthogonal to the third axis A3. The support body 101 may rotate about the fourth axis A4, and simultaneously perform a translational motion with respect to the proximal support 91 of FIG. 2. Thus, the support body 101 and the distal support 92 connected thereto may rotate about the RCM in the vicinity of the talocrural joint of the user.

The first elastic body 16a may connect the support joint 102 and the second drive link 12. A first end of the first elastic body 16a may be supported by the upward protrusion 103a of the support joint 102, and a second end of the first elastic body 16a may be supported by the link projection 123 of the second drive link 12.

The first elastic body 16a may be compressed or extended based on an angle at which the support joint 102 rotates about the third axis A3. When the subtalar joint of the user is in an initial state, the first elastic body 16a may have an initial length. When the subtalar joint of the user performs an inversion motion or an eversion motion, the support joint 102 may rotate with respect to the second drive link 12, and the first elastic body 16a may be extended. As an angle of the inversion motion or the eversion motion of the subtalar joint of the user increases, the first elastic body 16a may apply a greater elastic force to the support joint 102 such that the support joint 102 may return to the initial state. By the above structure, the motion assistance apparatus 1 may prevent a twist of the foot of the user when the user walks.

Hereinafter, "second elastic body" and "inversion elastic body" are used interchangeably. And, "third elastic body" and "eversion elastic body" are used interchangeably.

Figure 9:
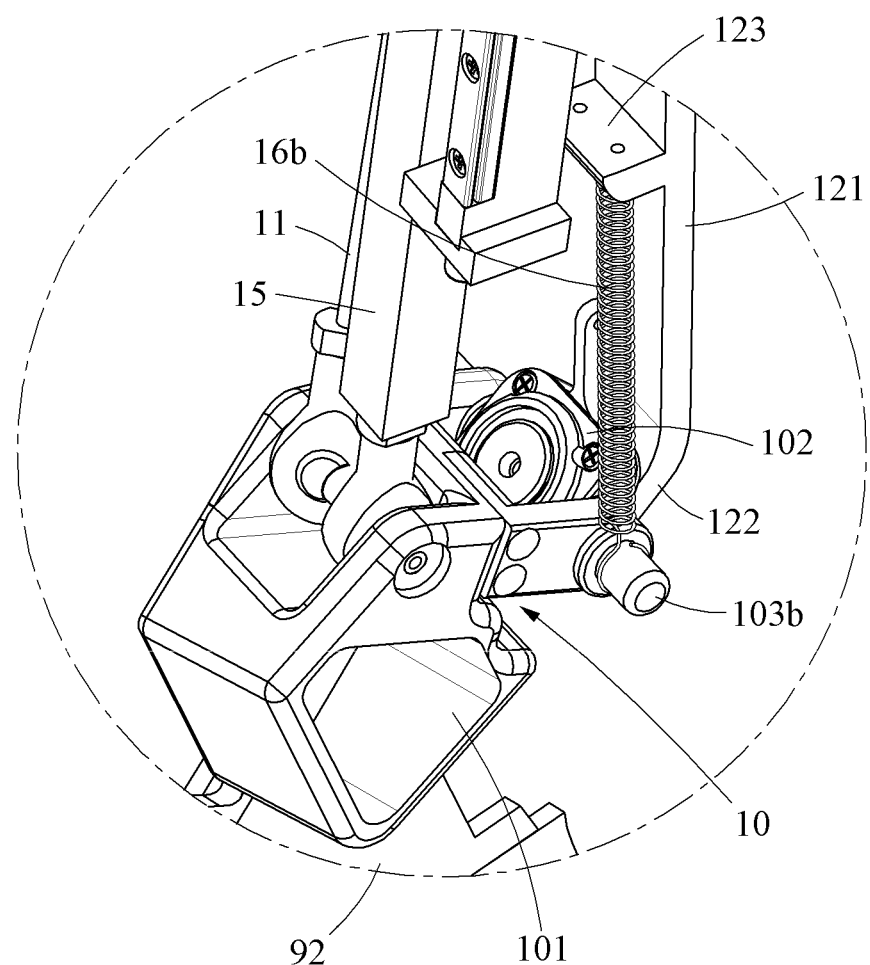
FIG. 9 is a partially enlarged perspective view illustrating a motion assistance apparatus according to at least one example embodiment.

FIG. 9 is a partially enlarged perspective view illustrating a motion assistance apparatus according to at least one example embodiment.

Referring to FIG. 9, the motion assistance apparatus 1 may include the inversion elastic body 16b connecting the inversion protrusion 103b and the second drive link 12. Further, when the support body 101 is in a neutral state, the inversion elastic body 16b may have an initial length.

Meanwhile, based on the initial state, a virtual plane including the rotation axis A3 of the support joint 102 (see FIG. 8) and being perpendicular to the rotation axis A4 of the support body 101 (see FIG. 8) may be assumed. In this example, as shown in FIG. 9, a distance from the virtual plane to a portion of the inversion elastic body 16b connected to the inversion protrusion 103b may be greater than a distance from the virtual plane to a portion of the inversion elastic body 16b connected to the second drive link 12. By the above structure, the length of the inversion elastic body 16b may change more greatly when the inversion motion is performed, than when the eversion motion is performed at the same angle. That is, the inversion elastic body 16b may provide a greater elastic restoring force when the user performs the inversion motion, than when the user performs the eversion motion. Thus, an elastic restoring force provided when the inversion motion is performed and an elastic restoring force provided when the eversion motion is performed may be set differently, whereby the motion assistance apparatus 1 may assist a stroke patient, who is likely to perform an abnormal inversion motion in a swing phase, to walk normally.

Figure 10:
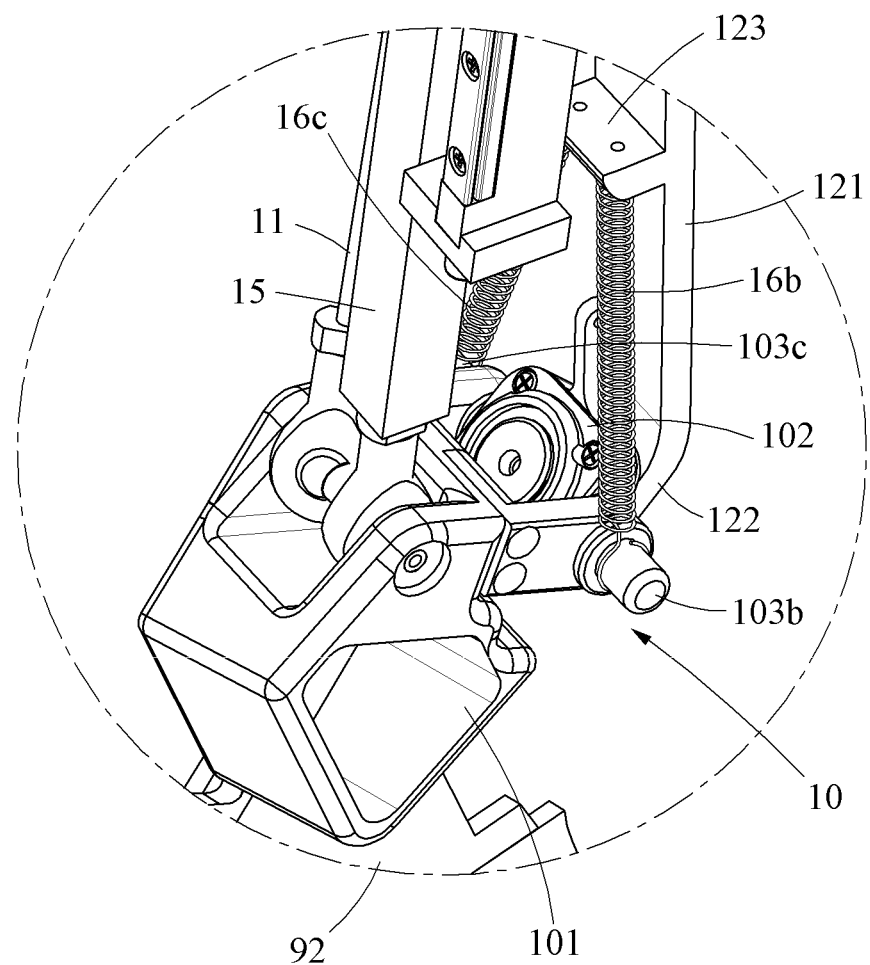
FIG. 10 is a partially enlarged perspective view illustrating a motion assistance apparatus according to at least one example embodiment.

FIG. 10 is a partially enlarged perspective view illustrating a motion assistance apparatus according to at least one example embodiment.

Referring to FIG. 10, the motion assistance apparatus 1 may include the inversion elastic body 16b and the eversion elastic body 16c coupled to different portions of the support link 10. A first end of the inversion elastic body 16b may be supported by the inversion protrusion 103b, and a second end of the inversion elastic body 16b may be supported by the second drive link 12. A first end of the eversion elastic body 16c may be supported by the eversion protrusion 103c, and a second end of the eversion elastic body 16c may be supported by the second drive link 12.

The inversion elastic body 16b and the eversion elastic body 16c may adjust a magnitude of an elastic force applied to the foot rotating about the subtalar joint. Meanwhile, by setting an elasticity coefficient of the inversion elastic body 16b to be higher than an elasticity coefficient of the eversion elastic body 16c, an unintended inversion motion may be prevented efficiently. It is also obvious that the elasticity coefficient of the inversion elastic body 16b may be equal to the elasticity coefficient of the eversion elastic body 16c, or the elasticity coefficient of the eversion elastic body 16c may be higher than the elasticity coefficient of the inversion elastic body 16b. The elasticity coefficients of the inversion elastic body 16b and the eversion elastic body 16c may be selected to be suitable for a state of the user.

Meanwhile, as necessary, one of the inversion elastic body 16b and the eversion elastic body 16c may be omitted.

Figure 11:
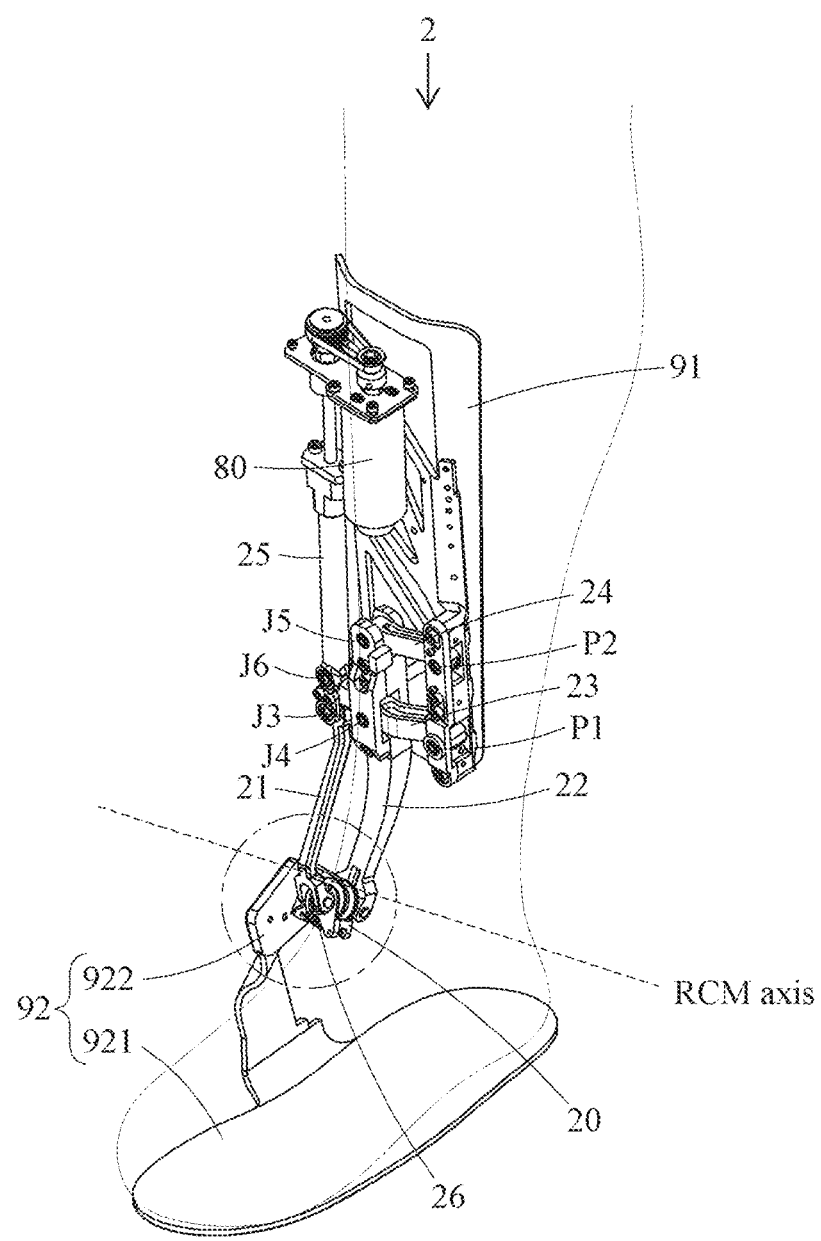
FIG. 11 is a perspective view illustrating a motion assistance apparatus according to at least one example embodiment.
Figure 12:
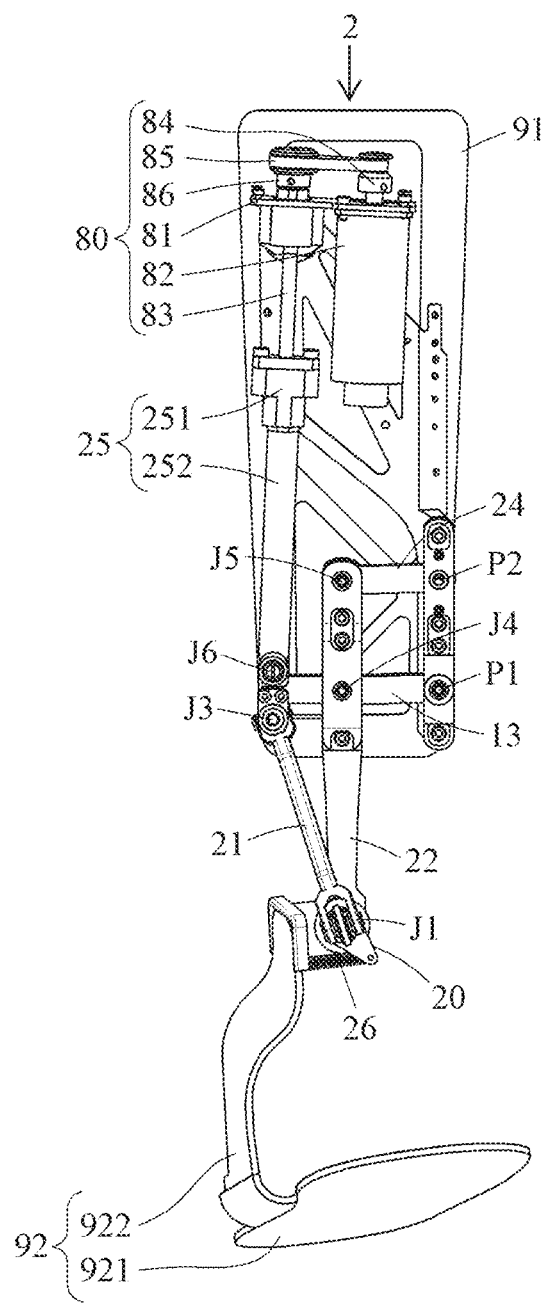
FIG. 12 is a front view illustrating a motion assistance apparatus according to at least one example embodiment.
Figure 13:
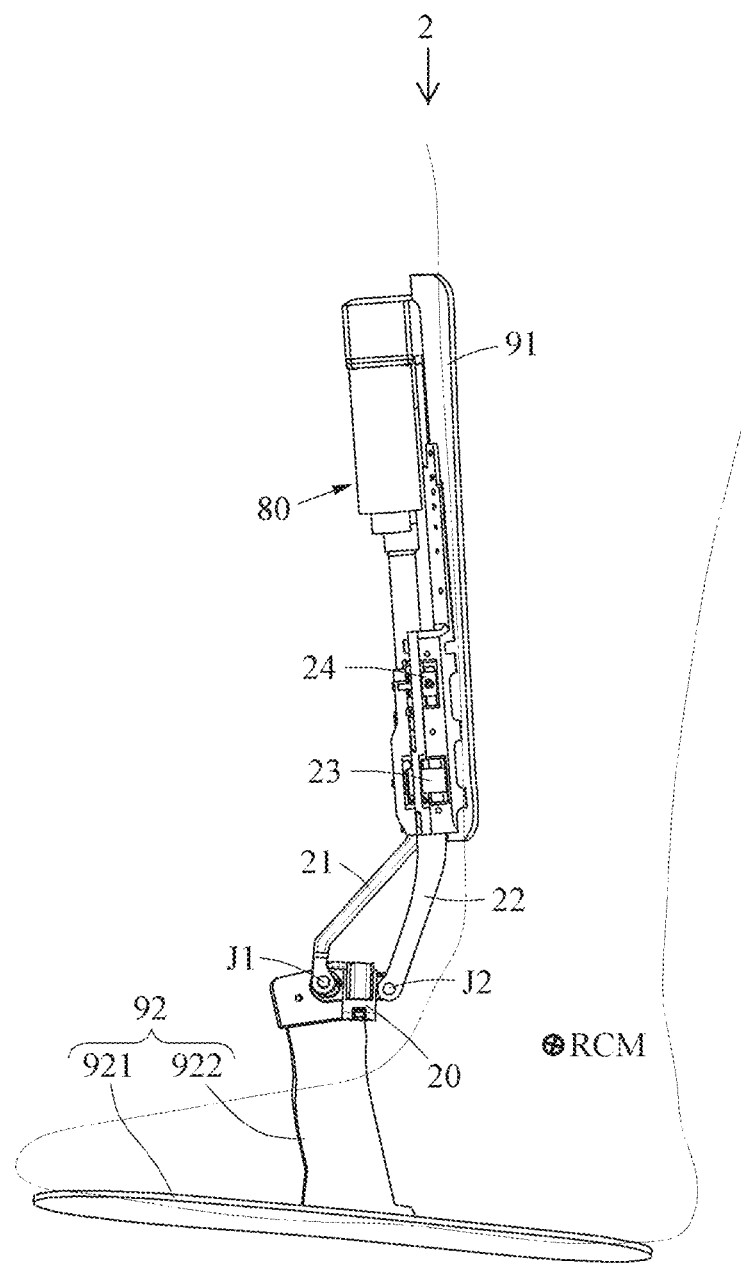
FIG. 13 is a side view illustrating a user wearing a motion assistance apparatus according to at least one example embodiment.
Figure 14:
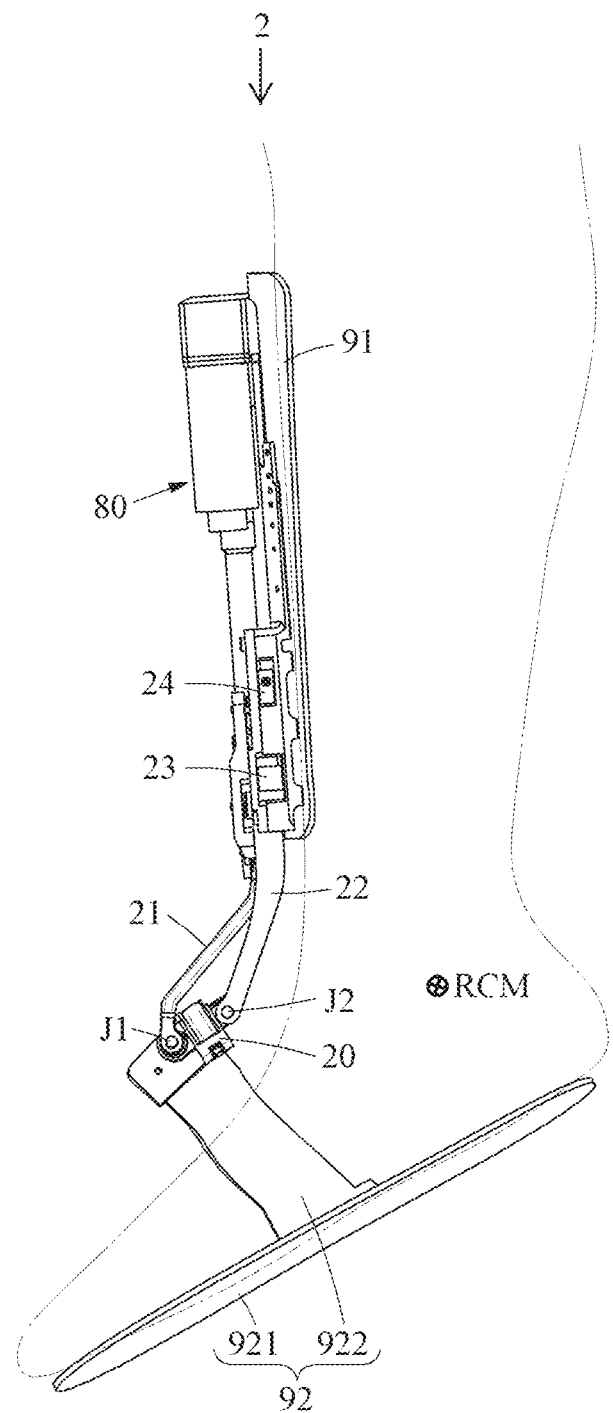
FIG. 14 is a side view illustrating a plantar-flexion motion of a user wearing a motion assistance apparatus according to at least one example embodiment.
Figure 15:
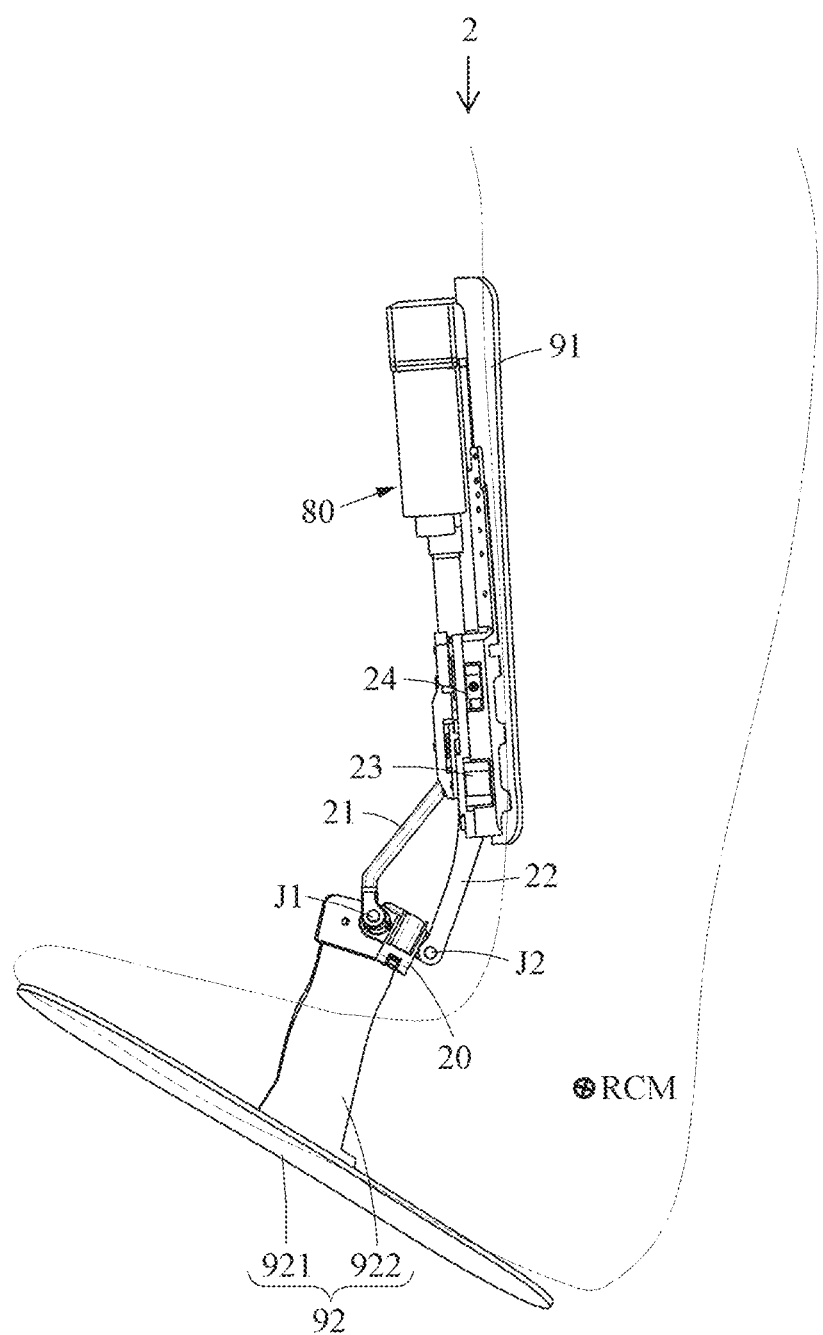
FIG. 15 is a side view illustrating a dorsi-flexion motion of a user wearing a motion assistance apparatus according to at least one example embodiment.

FIG. 11 is a perspective view illustrating a motion assistance apparatus according to at least one example embodiment, FIG. 12 is a front view illustrating the motion assistance apparatus according to at least one example embodiment, and FIG. 13 is a side view illustrating a user wearing the motion assistance apparatus according to at least one example embodiment. FIG. 14 is a side view illustrating a plantar-flexion motion of the user wearing the motion assistance apparatus according to at least one example embodiment, and FIG. 15 is a side view illustrating a dorsi-flexion motion of the user wearing the motion assistance apparatus according to at least one example embodiment.

Referring to FIGS. 11 through 15, a motion assistance apparatus 2 may include the proximal support 91, the distal support 92, a support link 20, a first drive link 21, a second drive link 22, a coupling link 23, a connecting link 24, a power transmitting rod 25, an elastic body 26, and the actuator 80.

The distal support 92 may include the insole part 921 and the connecting part 922.

The connecting part 922 may be rotatably connected to the support link 20 along a circumference of the support link 20. In this example, the user may perform an inversion motion and/or an eversion motion of a talocalcaneal joint while wearing the motion assistance apparatus 2.

The support link 20 may simultaneously perform a translational motion and a rotational motion with respect to the proximal support 91. The support link 20 may rotate about an RCM. The support link 20 may transmit the power to the distal support 92. When the support link 20 rotates about the RCM, the distal support 92 connected to the support link 20 may also rotate about the RCM.

Both ends of the support link 20 may be rotatably connected to the first drive link 21 and the second drive link 22, respectively. As shown in FIG. 13, a first end of the support link 20 may be connected to the first drive link 21 by a first joint J1, and a second end of the support link 20 may be connected to the second drive link 22 by a second joint J2. Any one or any combination of the first joint J1 and the second joint J2 may be a joint that implements a 2-DOF rotational motion. As shown in the drawings, the first joint J1 may be a universal joint or a ball joint that enables the support link 20 and the first drive link 21 to rotate with 2-DOF. The second joint J2 may be a joint that enables the support link 20 and the second drive link 22 to rotate with 1-DOF, for example, a hinge. By the above connection relationship, an angle between the first drive link 21 and the second drive link 22 projected respectively in a frontal plane (see FIG. 2) and a sagittal plane (see FIG. 3) may change simultaneously based on driving of the actuator 80.

The support link 20 may have a cylindrical shape, and the connecting part 922 may be rotatably connected to a circumferential surface of the cylindrical shape. For example, outer flanges may be at both ends of the support link 20, and prevent a separation of the connecting part 922 from the support link 20.

The first drive link 21 may connect the support link 20 and the coupling link 23. The first drive link 21 may be rotatably connected to the support link 20 by the first joint J1, and rotatably connected to the coupling link 23 a third joint J3. The third joint J3 may be a joint that implements a 2-DOF rotational motion. For example, the third joint J3 may be a universal joint or a ball joint.

The second drive link 22 may connect the support link 20, the coupling link 23, and the connecting link 24. The second drive link 22 may be rotatably connected to the support link 20 by the second joint J2, rotatably connected to the coupling link 23 by a fourth joint J4, and rotatably connected to the connecting link 24 by a fifth joint J5.

The coupling link 23 may couple the first drive link 21 and the second drive link 22. The coupling link 23 may rotate about a first point P1 on the proximal support 91. The coupling link 23 may be rotatably connected to the first drive link 21 by the third joint J3, and rotatably connected to the second drive link 22 by the fourth joint J4. When the coupling link 23 rotates, each of the first drive link 21 and the second drive link 22 may perform a translational motion with respect to the proximal support 91. A distance between the third joint J3 and the first point P1 may be greater than a distance between the fourth joint J4 and the first point P1. That is, based on the first point P1, a radius of gyration of the third joint J3 may be greater than a radius of gyration of the fourth joint J4. When the coupling link 23 rotates, the first drive link 21 may perform the translational motion at a faster velocity than the second drive link 22. Meanwhile, the first drive link 21 may simultaneously perform the translational motion and a rotational motion with respect to the proximal support 91.

The coupling link 23 may be installed to perform a rotational motion on a plane parallel to the frontal plane of the user when the user wears the motion assistance apparatus 2. In this example, a protruding height of the entire motion assistance apparatus 2 from the shank of the user may be reduced.

Meanwhile, unlike the drawings, the coupling link 23 may be installed to perform a rotational motion on a plane parallel to the sagittal plane of the user. In this example, any one or any combination of the first joint J1 and the third joint J3 may be configured as a joint having a 1-DOF of rotation, for example, a hinge.

The connecting link 24 may rotate about a second point P2 on the proximal support 91. The connecting link 24 may be rotatably connected to the second drive link 22 by the fifth joint J5. The connecting link 24 may be parallel to the coupling link 23, and a distance from the first point P1 to the fourth joint J4 may be equal to a distance from the second point P2 to the fifth joint J5. In this example, the second drive link 22 may move while being parallel to a virtual line connecting the first point P1 and the second point P2.

The connecting link 24 may be installed to perform a rotational motion on the plane parallel to the frontal plane of the user when the user wears the motion assistance apparatus 2. By the above structure, the protruding height of the entire motion assistance apparatus 2 from the shank of the user may be reduced.

Meanwhile, unlike the above, when the coupling link 23 is installed to perform a rotational motion on the plane parallel to the sagittal plane of the user, the connecting link 24 may also be installed to perform a rotational motion on the plane parallel to the sagittal plane of the user similarly.

The first joint J1 may be in front of the second drive link 22. When viewing the motion assistance apparatus 2 from a side as in FIG. 13, the first drive link 21 may be in front of the second drive link 22. By the above structure, although the coupling link 23 and the connecting link 24 perform the rotational motions on the plane parallel to the frontal plane of the user, the support link 20 may rotate about the RCM in rear of the second drive link 22.

The support link 20, the first drive link 21, the second drive link 22, the coupling link 23, and the connecting link 24 may move with 1-DOF. That is, by driving one of the support link 20, the first drive link 21, the second drive link 22, the coupling link 23 and the connecting link 24, the distal support 92 may be driven.

The actuator 80 may move one of the support link 20, the first drive link 21, the second drive link 22, the coupling link 23, and the connecting link 24. The actuator 80 may pull the first drive link 21 toward the actuator 80 to assist a dorsiflexion motion of the foot of the user, or push the first drive link 21 away from the actuator 80 to assist a plantar-flexion motion of the foot of the user. The actuator 80 may include the drive housing 81, the drive motor 82, the guide 83, a drive shaft 84 configured to rotate using a driving power of the drive motor 82, a power transmitting member 85 configured to move in response to the rotation of the drive shaft 84, and a power receiver 86 configured to move the power transmitting rod 25 upward and downward in the manner of a ball screw by receiving a power from the power transmitting member 85.

The power transmitting rod 25 may include a power transmitting body 251 and an extension 252. The coupling link 23 may be rotatably connected to the extension 252 by a sixth joint J6. The sixth joint J6 may be a joint that enables the coupling link 23 to rotate with respect to the extension 252 with 1 DOF, for example a hinge.

The motion assistance apparatus 1 may further include a controller (not shown) that includes memory and processing circuitry.

The memory may include at least one of a volatile memory, non-volatile memory, random access memory (RAM), a flash memory, a hard disk drive, and an optical disk drive.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design or execution of computer readable instructions stored in a memory (not shown), as a special purpose computer to control the actuator 80.

For example, the processing circuitry may be configured to control the drive motor 82 to generate the power to drive the power transmitting rod 15 such that the generated power is transmitted to distal support 92.

Further, as discussed in more detail below, with respect to FIG. 24, in some example embodiments, the controller configured to control the actuator 80 may also control the sub-actuator 70. However, example embodiments are not limited thereto. For example, in some other example embodiments, the sub-actuator 70 may be controlled by a discrete controller.

The elastic body 26 may connect the support link 20 and the distal support 92, and deform when the distal support 92 rotates about the support link 20. When the distal support 92 is out of the initial state and performs an inversion motion or an eversion motion about the support link 20, the elastic body 26 may apply a restoring force to the distal support 92 such that the distal support 92 may return to the initial state.

Figure 16:
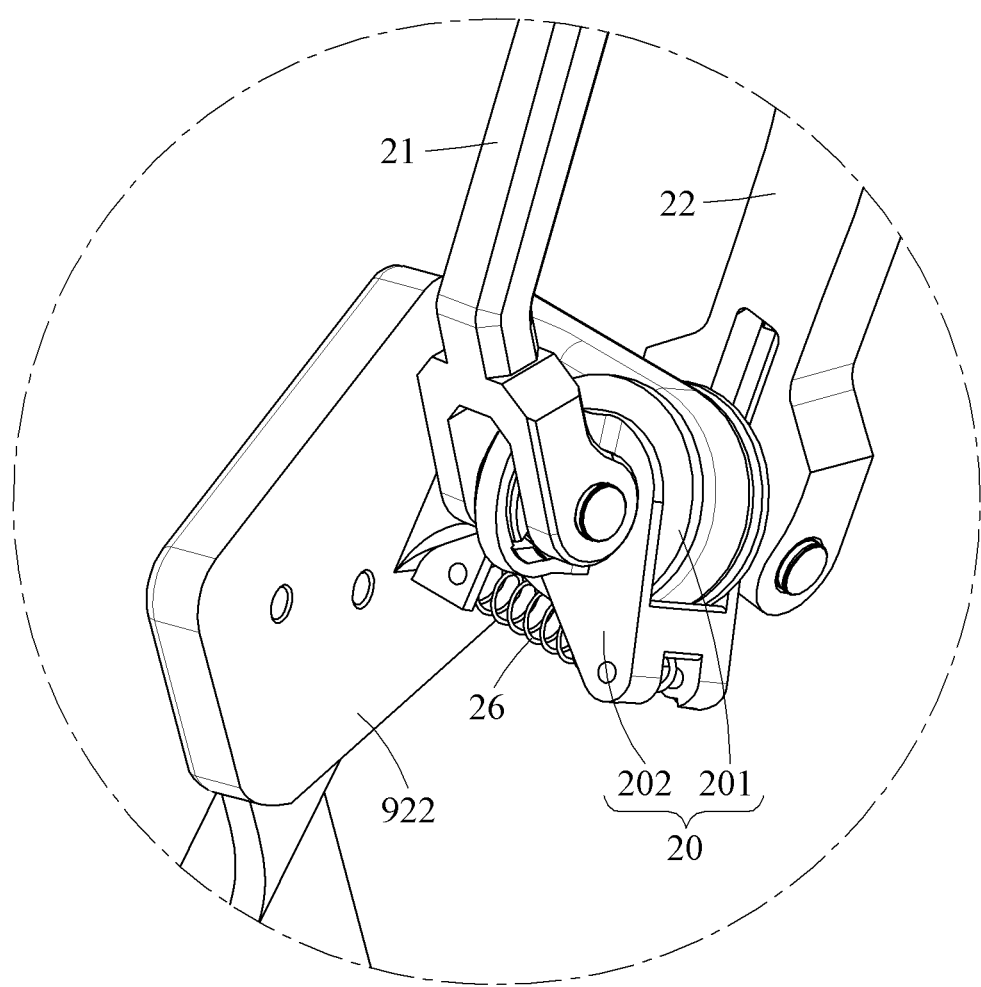
FIG. 16 is a partially enlarged perspective view illustrating a motion assistance apparatus according to at least one example embodiment.
Figure 17:
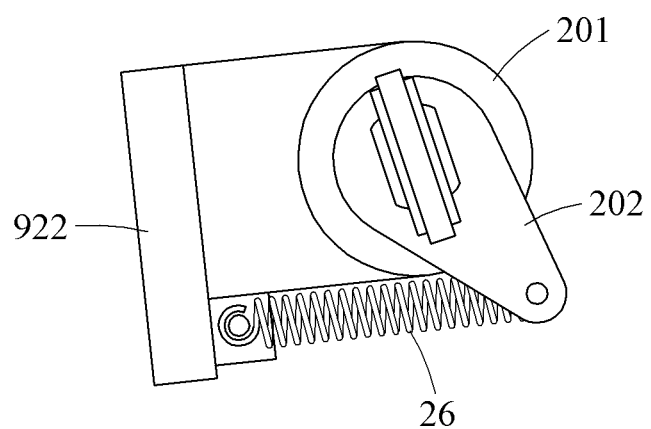
FIG. 17 is a plan view illustrating a neutral state of a distal support according to at least one example embodiment.
Figure 18:
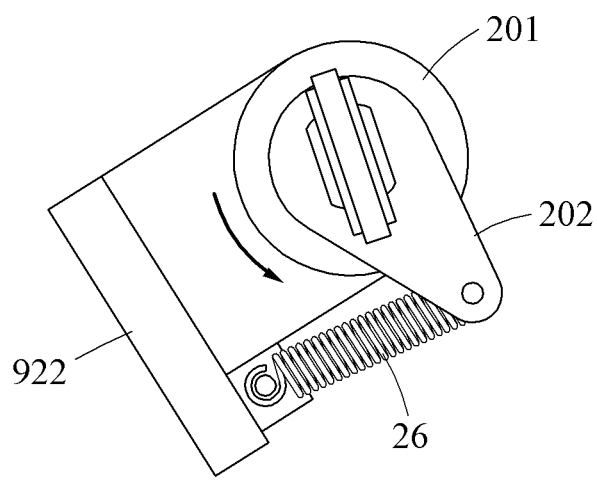
FIG. 18 is a plan view illustrating a support link and a distal support in a state in which a foot of a user performs an inversion motion according to at least one example embodiment.
Figure 19:
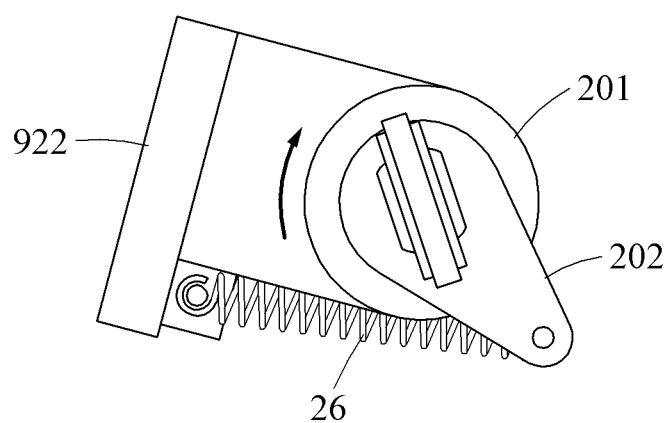
FIG. 19 is a plan view illustrating a support link and a distal support in a state in which a foot of a user performs an eversion motion according to at least one example embodiment.

FIG. 16 is a partially enlarged perspective view illustrating a motion assistance apparatus according to at least one example embodiment, FIG. 17 is a plan view illustrating a neutral state of a distal support according to at least one example embodiment, FIG. 18 is a plan view illustrating a support link and the distal support in a state in which a foot of a user performs an inversion motion according to at least one example embodiment, and FIG. 19 is a plan view illustrating the support link and the distal support in a state in which the foot of the user performs an eversion motion according to at least one example embodiment.

Referring to FIGS. 16 through 19, the support link 20 may include a support body 201 configured to connect the first drive link 21 and the second drive link 22, and a protrusion 202 protruding from the support body 201 toward a first side thereof. The support body 201 and the protrusion 202 may be fixed as an integral body. When the user wears the motion assistance apparatus 2, the protrusion 202 may protrude toward an inner portion of the foot of the user. The protrusion 202 may support a first end of the elastic body 26.

The connecting part 922 of the distal support 92 of FIG. 11 may rotate about the support body 201. The connecting part 922 may enclose the support body 201. When the user wears the motion assistance apparatus 2, the connecting part 922 may cover an outer side of the foot of the user. The connecting part 922 may support a second end of the elastic body 26.

The elastic body 26 may connect the protrusion 202 and the connecting part 922. When the connecting part 922 rotates about the support body 201, the elastic body 26 may be extended or compressed. The elastic body 26 may be compressed when the foot of the user performs an inversion motion about the subtalar joint, and may be extended when the foot of the user performs an eversion motion about the subtalar joint.

Figure 20:
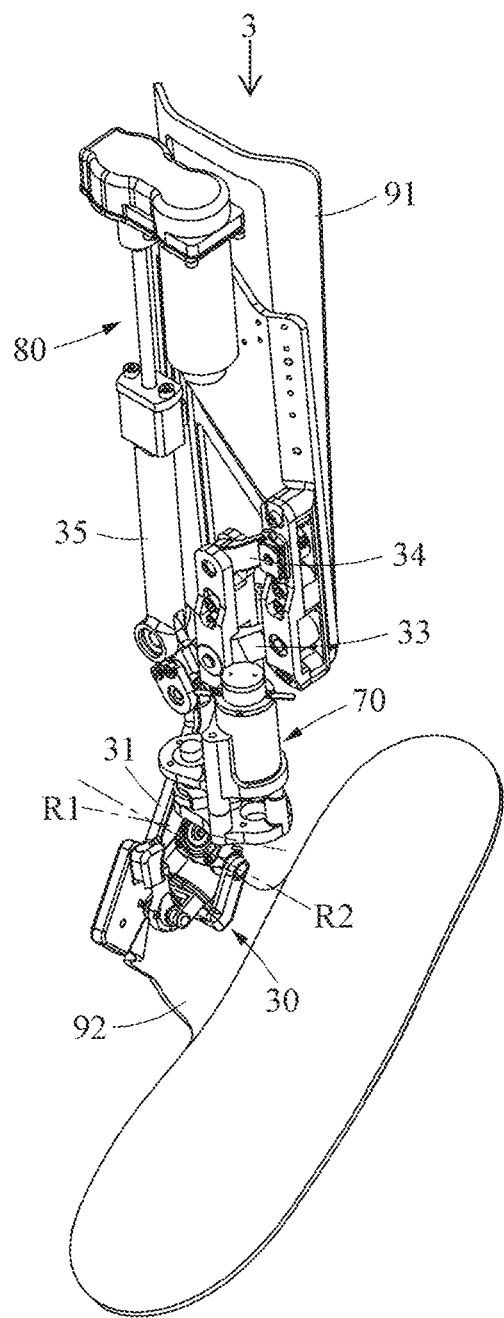
FIG. 20 is a perspective view illustrating a motion assistance apparatus according to at least one example embodiment.
Figure 21:
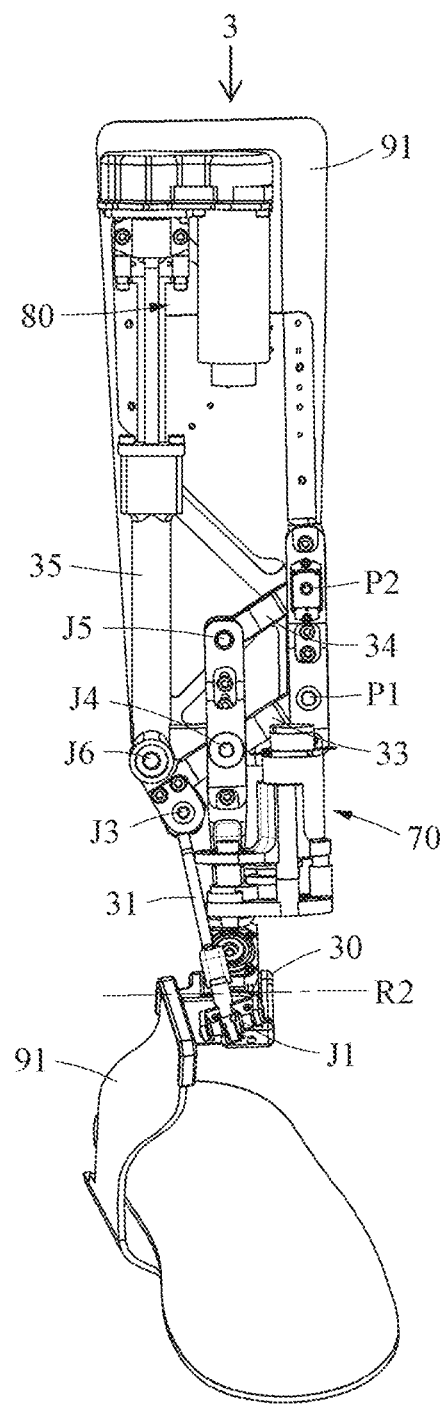
FIG. 21 is a front view illustrating a motion assistance apparatus according to at least one example embodiment.
Figure 22:
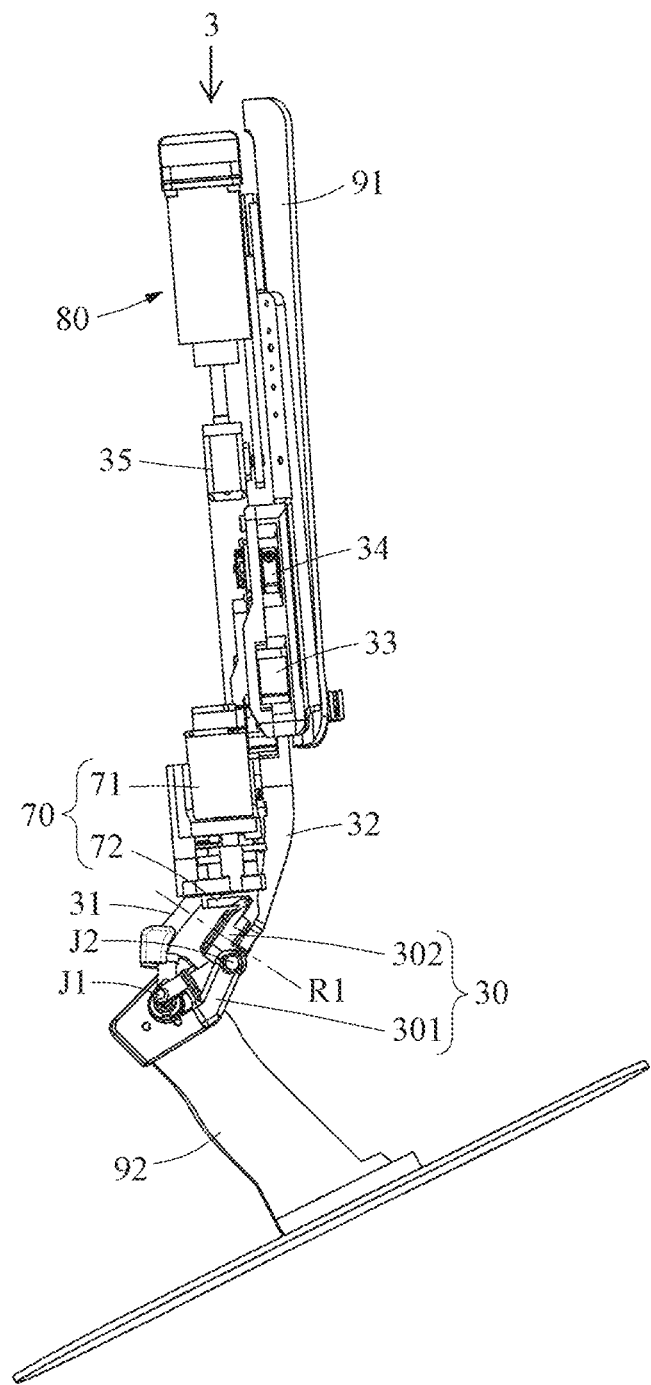
FIG. 22 is a side view illustrating a motion assistance apparatus according to at least one example embodiment.
Figure 23:
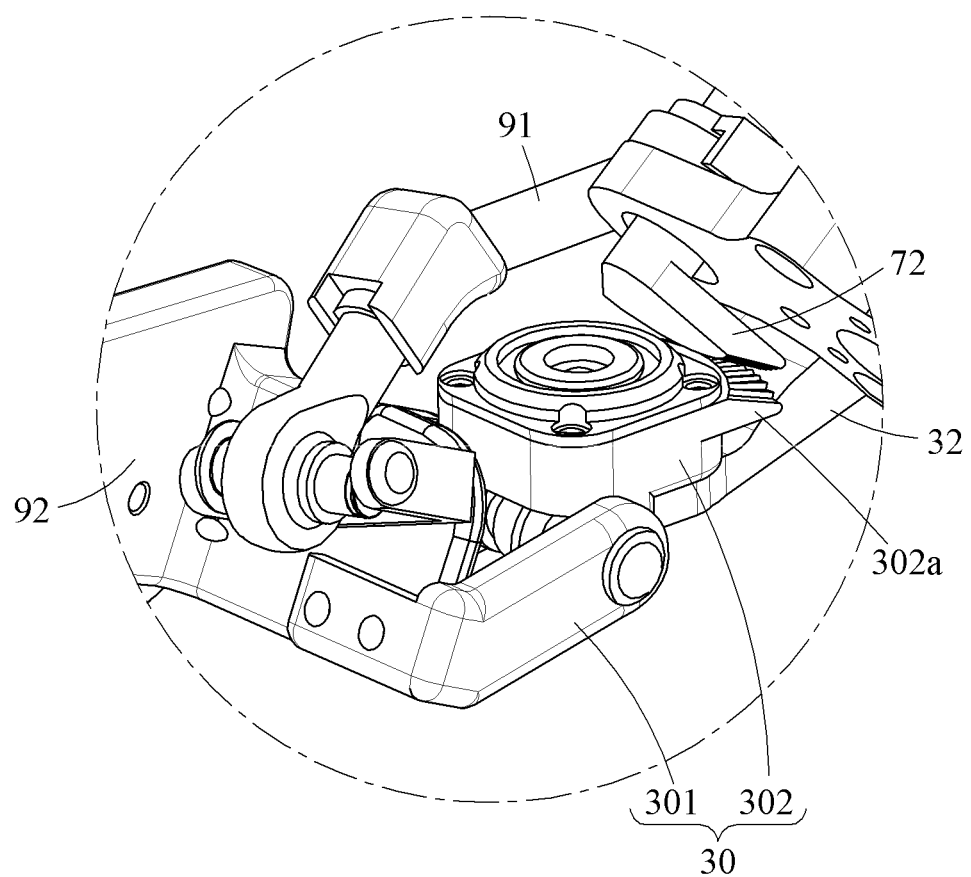
FIG. 23 is a partially enlarged perspective view illustrating a sub-bevel gear of a support link engaging with a sub-bevel gear of a sub-actuator in a motion assistance apparatus according to at least one example embodiment.
Figure 24:
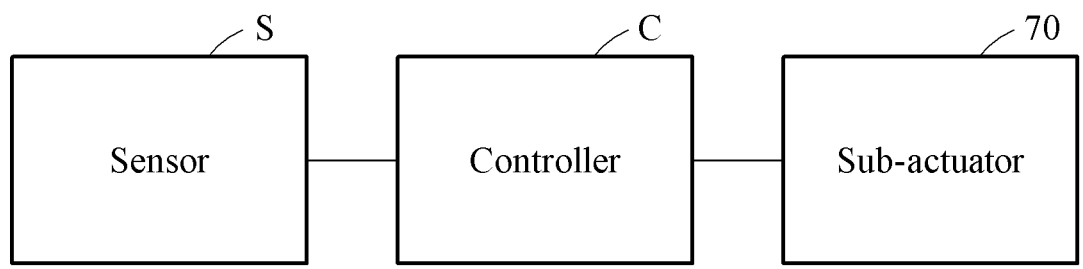
FIG. 24 is a block diagram illustrating a process of controlling a sub-actuator of a motion assistance apparatus according to at least one example embodiment.

FIG. 20 is a perspective view illustrating a motion assistance apparatus according to at least one example embodiment, FIG. 21 is a front view illustrating the motion assistance apparatus according to at least one example embodiment, FIG. 22 is a side view illustrating the motion assistance apparatus according to at least one example embodiment, FIG. 23 is a partially enlarged perspective view illustrating a sub-bevel gear of a support link engaging with a sub-bevel gear of a sub-actuator in the motion assistance apparatus according to at least one example embodiment, and FIG. 24 is a block diagram illustrating a process of controlling the sub-actuator of the motion assistance apparatus according to at least one example embodiment.

Referring to FIGS. 20 through 24, a motion assistance apparatus 3 may include the proximal support 91, the distal support 92, a support link 30, a first drive link 31, a second drive link 32, a coupling link 33, a connecting link 34, a power transmitting rod 35, a sensor S, a controller C, a sub-actuator 70, and a main actuator 80.

The support link 30 may simultaneously perform a translational motion and a rotational motion with respect to the proximal support 91, thereby rotating about an RCM. The support link 30 may include a support body 301 and a support joint 302.

The support joint 302 may be rotatably connected to the second drive link 32 about a first rotation axis R1. The first rotation axis R1 may be the same as or parallel to the second axis A2 of FIG. 2 which is an axis about which the subtalar joint of the user performs an inversion motion and an eversion motion. The support joint 302 may rotate using a power received from the sub-actuator 70. A power transmitting structure between the sub-actuator 70 and the support joint 302 may include various types of known power transmitting structures, for example, various types of gears, wires, rolling friction structures, or universal joints. For example, the support joint 302 may include a first sub-bevel gear 302a protruding upward.

The support body 301 may be rotatably connected to the support joint 302 about a second rotation axis R2. The second rotation axis R2 may intersect the first rotation axis R1. The second rotation axis R2 may be the same or parallel to the first axis A1 of FIG. 1A about which the talocrural joint of the user performs a plantar-flexion motion and a dorsi-flexion motion.

The sub-actuator 70 may rotate the support joint 302 about the first rotation axis R1. The sub-actuator 70 may be connected to the second drive link 32. The sub-actuator 70 may include a sub-driving source 71 and a second sub-bevel gear 72.

The sub-driving source 71 may generate a power to rotate the support joint 302. The sub-driving source 71 may rotate the second sub-bevel gear 72 engaging with the first sub-bevel gear 302a of the support joint 302.

As shown in FIG. 23, an angle between shafts of the first sub-bevel gear 302a and the second sub-bevel gear 72 may be greater than 90 degrees. In this example, the sub-actuator 70 may be parallel to a longitudinal direction of the proximal support 91, whereby a protruding height of the sub-actuator 70 from the proximal support 91 may be reduced, and thus the entire motion assistance apparatus 3 may be provided in a compact size while reducing an inertial moment.

The sensor S may sense motion state information of the user. The sensor S may sense an angle between the support joint 302 and the second drive link 32, thereby sensing an eversion motion or an inversion motion of the user. In an example, the sensor S may be an encoder between the support joint 302 and the second drive link 32. In another example, the sensor S may be an inertial measurement unit (IMU) sensor mounted on the proximal support 91, or an encoder that measures an angle between a pair of links rotatably connected to a vicinity of a hip joint of the user, and may sense whether a leg of the user is in a swing phase or a stance phase. The above types of the sensor S are merely some examples. Various types of sensors may be used to measure the motion state information of the user.

The controller C may control the sub-actuator 70 based on the motion state information of the user sensed by the sensor S. In an example, in response to sensing of an inversion motion or an eversion motion performed at a desired (or, alternatively, a predetermined) or greater angle by the foot of the user, the controller C may control the sub-actuator 70 to restore a posture of the foot of the user. In another example, when the leg of the user is in a stance phase, the controller C may control the sub-actuator 70 to enable the foot of the user to be in a neutral state. A foot of a normal user may be in an inversion state by a set (or, alternatively, a predetermined) angle in a swing phase, whereas a foot of a stroke patient may be in an inversion state at an angle overly exceeding the set (or, alternatively, the predetermined) angle. Thus, when the leg of the user is in the swing phase, the controller C may control the sub-actuator 70 to enable the foot of the user to be in an inversion state at the set angle rather than at the angle overly exceeding the same.

In some example embodiments, one or more of the elastic bodies 16a, 16b, 16c, and 26 and the sub-actuator 70 may be collectively referred to as a "torque providing device". The torque providing device may provide a torque to rotate a support joint passively or actively.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus, comprising:
    a proximal support configured to support a proximal part of a user;
    a first drive link and a second drive link, the first drive link configured to perform a translational motion with respect to the proximal support at a first velocity and the second drive link configured to perform a translational motion with respect to the proximal support at a second velocity, the first velocity being different from the second velocity;
    a support link configured to rotate about a remote center of motion (RCM) in a vicinity of a joint of the user between the proximal part and the distal part of the user while the support link is positioned on a front side of the user when the user wears the motion assistance apparatus, the support link including,
        a support joint rotatably connected to the second drive link, and
        a support body connecting the first drive link and the support joint connected to the second drive link such that, in response to the first drive link and the second drive link performing the translational motion with respect to the proximal support at the first velocity and the second velocity, respectively, the support body is configured to simultaneously perform a translational motion and a rotational motion with respect to the proximal support to rotate the support link about the RCM;
    a distal support connected to the support body, the distal support configured to support a distal part of the user; and
    a torque providing device connected to the second drive link, the torque providing device configured to provide a torque to rotate the support joint.

2. The motion assistance apparatus of claim 1, further comprising:
    a coupling link rotatably connected to the proximal support, first drive link and the second drive link, the coupling link configured to rotate about the proximal support; and
    a connecting link rotatably connected to the proximal support and the second drive link, the connecting link configured to rotate about the proximal support, wherein
        the first velocity is greater than the second velocity such that the first drive link is configured to perform the translation motion with respect to the proximal support at a faster velocity than the second drive link.

3. The motion assistance apparatus of claim 1, wherein the torque providing device comprises:
    an elastic body configured to deform in response to rotation of the support joint about the second drive link.

4. The motion assistance apparatus of claim 3, further comprising:
    an upward protrusion configured to protrude from the support joint, wherein
        the elastic body is configured to connect the upward protrusion of the support joint and the second drive link.

5. The motion assistance apparatus of claim 3, further comprising:
    an inversion protrusion configured to protrude from the support joint in an inward direction of the user, the inward direction extending towards a sagittal plane of the user, wherein
        the elastic body includes an inversion elastic body configured to connect the inversion protrusion of the support joint and the second drive link.

6. The motion assistance apparatus of claim 5, further comprising:
    an eversion protrusion configured to protrude from the support joint in an outward direction of the user, the outward direction extending away from the sagittal plane of the user, wherein
        the elastic body further includes an eversion elastic body configured to connect the eversion protrusion of the support joint and the second drive link.

7. The motion assistance apparatus of claim 6, wherein an elasticity coefficient of the inversion elastic body is greater than an elasticity coefficient of the eversion elastic body.

8. The motion assistance apparatus of claim 1, wherein the torque providing device comprises:
    a sub-actuator configured to provide a rotational power to the support joint to rotate the support joint.

9. The motion assistance apparatus of claim 8, wherein
    the support joint includes a first sub-bevel gear, and
    the sub-actuator includes a second sub-bevel gear, the second sub-bevel gear configured to engage with the first sub-bevel gear.

10. The motion assistance apparatus of claim 9, wherein the sub-actuator is parallel to a longitudinal direction of the proximal support.

11. The motion assistance apparatus of claim 10, wherein an angle between a shaft of the first sub-bevel gear and a shaft of the second sub-bevel gear is greater than 90 degrees.

12. The motion assistance apparatus of claim 8, further comprising:
    a sensor configured to sense motion state information of the user; and
    a controller configured to control the sub-actuator based on the motion state information.

13. The motion assistance apparatus of claim 1, further comprising:
    an actuator rotatably connected to the proximal support, the actuator configured to generate power; and
    a power transmitting rod configured to transmit the power from the actuator to the support body.

14. The motion assistance apparatus of claim 13, wherein the actuator comprises:
- a drive housing rotatably connected to the proximal support;
- a drive motor attached to the drive housing, the drive motor configured to generate the power; and
- a guide configured to extend from the drive housing, and to guide sliding of the power transmitting rod.

15. The motion assistance apparatus of claim 1, wherein the RCM is in a vicinity of a talocrural joint of the user when the user wears the motion assistance apparatus.

16. A motion assistance apparatus, comprising:
- a proximal support;
- a first drive link and a second drive link, the first drive link configured to perform a translational motion with respect to the proximal support at a first velocity and the second drive link configured to perform a translational motion with respect to the proximal support at a second velocity, the first velocity being different from the second velocity;
- a support link configured to rotate about a remote center of motion (RCM) in a vicinity of a joint of the user while the support link is positioned on a front side of the user when the user wears the motion assistance apparatus, the support link including a support body having a first end and a second end, the first end of the support body and the second end of the support body rotatably connected to the first drive link and the second drive link, respectively, such that, in response to the first drive link and the second drive link performing the translational motion with respect to the proximal support at the first velocity and the second velocity, respectively, the support body is configured to simultaneously perform a translational motion and a rotational motion with respect to the proximal support to rotate the support link about the RCM;
- a distal support rotatably connected to the support body; and
- a torque providing device connected to the second drive link, the torque providing device configured to provide a torque to rotate the distal support.

17. The motion assistance apparatus of claim 16, wherein the torque providing device comprises:
- an elastic body configured to connect the support body and the distal support, and to deform in response to rotation of the distal support about the support body.

18. The motion assistance apparatus of claim 17, further comprising:
- a protrusion configured to protrude from the support body toward an inner portion of a foot of a user, the protrusion configured to support a first end of the elastic body, wherein
- the distal support includes a connecting part configured to cover an outer portion of the foot of the user, and to support a second end of the elastic body.

* * * * *